United States Patent
Hajjarian et al.

(10) Patent No.: US 9,664,606 B2
(45) Date of Patent: May 30, 2017

(54) COMPENSATION FOR CAUSES OF TEMPORAL FLUCTUATIONS OF BACKSCATTERED SPECKLE PATTERNS IN LASER SPECKLE RHEOLOGY OF BIOLOGICAL FLUIDS

(71) Applicants: Zeinab Hajjarian, Boston, MA (US); Seemantini K. Nadkarni, Boston, MA (US)

(72) Inventors: Zeinab Hajjarian, Boston, MA (US); Seemantini K. Nadkarni, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 134 days.

(21) Appl. No.: 14/428,506

(22) PCT Filed: Sep. 16, 2013

(86) PCT No.: PCT/US2013/059906
§ 371 (c)(1),
(2) Date: Mar. 16, 2015

(87) PCT Pub. No.: WO2014/043609
PCT Pub. Date: Mar. 20, 2014

(65) Prior Publication Data
US 2015/0276571 A1    Oct. 1, 2015

Related U.S. Application Data

(60) Provisional application No. 61/701,819, filed on Sep. 17, 2012, provisional application No. 61/738,808, filed on Dec. 18, 2012.

(51) Int. Cl.
*G01N 21/00*    (2006.01)
*G01N 11/02*    (2006.01)
(Continued)

(52) U.S. Cl.
CPC ............ *G01N 11/02* (2013.01); *G01N 21/41* (2013.01); *G01N 21/47* (2013.01);
(Continued)

(58) Field of Classification Search
CPC ... G01N 2203/0089; G01N 2203/0094; G01N 21/47; G01N 33/487; G01N 2291/02827;
(Continued)

(56) References Cited

U.S. PATENT DOCUMENTS

| | | | |
|---|---|---|---|
| 6,958,816 B1 * | 10/2005 | Dogariu | G01N 11/02 356/479 |
| 7,782,458 B2 * | 8/2010 | Snabre | G01N 15/0227 356/336 |

(Continued)

FOREIGN PATENT DOCUMENTS

| | | |
|---|---|---|
| DE | 10342604 A1 | 4/2004 |
| WO | 0138820 A1 | 5/2001 |
| WO | 2012112977 A1 | 8/2012 |

OTHER PUBLICATIONS

PCT International Search Report and Written Opinion, PCT/US2013/059906, Jan. 16, 2014.
(Continued)

*Primary Examiner* — Hoa Pham
(74) *Attorney, Agent, or Firm* — Quarles & Brady LLP

(57) ABSTRACT

An algorithm for determining viscoelastic modulus of an optically scattering biofluid that takes into account variable scattering and/or absorption characteristics of the biofluid. A correction to mean square displacement value charactetizing the Brownian motion of light scatterers is introduced based on a polarization-sensitive Monte-Carlo ray-tracing taking into account optical properties of the biofluid determined with the use of laser speckle rheology measurements. In contradistinction with a diffusion model, the correction-
(Continued)

implemented determination of the viscoelastic modulus applies to a biofluid with substantially any concentration of light-scattering particles.

18 Claims, 21 Drawing Sheets

(51) Int. Cl.
G01N 21/41 (2006.01)
G01N 21/47 (2006.01)
G01N 21/59 (2006.01)
G01N 33/487 (2006.01)

(52) U.S. Cl.
CPC ......... *G01N 21/4795* (2013.01); *G01N 21/59* (2013.01); *G01N 33/487* (2013.01); *G01N 2021/479* (2013.01); *G01N 2021/4769* (2013.01); *G01N 2021/4792* (2013.01); *G01N 2021/4797* (2013.01)

(58) Field of Classification Search
CPC ......... G01N 21/4795; G01N 2021/479; A61B 5/0069; A61B 5/02007
USPC ............ 356/450, 335–344; 436/63, 69, 164; 422/73, 82, 5, 82.09; 600/369
See application file for complete search history.

(56) References Cited

U.S. PATENT DOCUMENTS

| | | | | |
|---|---|---|---|---|
| 8,772,039 B2* | 7/2014 | Nadkarni | ........... | G01N 33/4905 422/73 |
| 2012/0307035 A1* | 12/2012 | Yaqoob | ................... | G01B 9/04 348/79 |
| 2013/0211748 A1* | 8/2013 | Itoh | ......................... | G01N 5/02 702/56 |
| 2014/0036272 A1* | 2/2014 | Nadkarni | ........... | G01N 21/4795 356/450 |
| 2014/0094666 A1* | 4/2014 | Fine | ..................... | A61B 5/7246 600/316 |
| 2014/0206980 A1* | 7/2014 | Lee | ...................... | A61B 5/0261 600/407 |
| 2014/0378845 A1* | 12/2014 | Nadkarni | ............. | A61B 5/0084 600/478 |
| 2015/0253240 A1* | 9/2015 | Rowe | ................. | G01B 9/02044 356/451 |
| 2017/0003271 A1* | 1/2017 | Nadkarmi | ............. | G01N 11/00 |

OTHER PUBLICATIONS

Cardinaux, et al., Microrheology of Giant-Micelle Solutions, Europhysics Letters, 2002, 57(5):738-744.

Hajjarian, et al., Intravascular Laser Speckle Imaging Catheter for the Mechanical Evaluation of the Arterial Wall, Journal of Biomedical Optics, 2011, 16(2):026005-1 thru 026005-7.

Hajjarian, et al., Evaluating the Viscoelastic Properties of Tissue from Laser Speckle Fluctuations, Scientific Reports, 2012, 2:316, pp. 1-8.

Hajjarian, et al., Evaluation and Correction for Optical Scattering Variations in Laser Speckle Rheology of Biological Fluids, PLOS One, 2013, 8(5):e65014, pp. 1-12.

Nadkarni, et al., Characterization of Atherosclerotic Plaques by Laser Speckle Imaging, Circulation, 2005, 112:885-892.

Nadkarni, et al., Measurement of Fibrous Cap Thickness in Atherosclerotic Plaques by Spatiotemporal Analysis of Laser Speckle Images, J. Biomed. Opt., 2006, 11(2):021006.

Nadkarni, et al., Laser Speckle Imaging of Atherosclerotic Plaques Through Optical Fiber Bundles, J. Biomed. Opt., 2008, 13(5):054016.

* cited by examiner

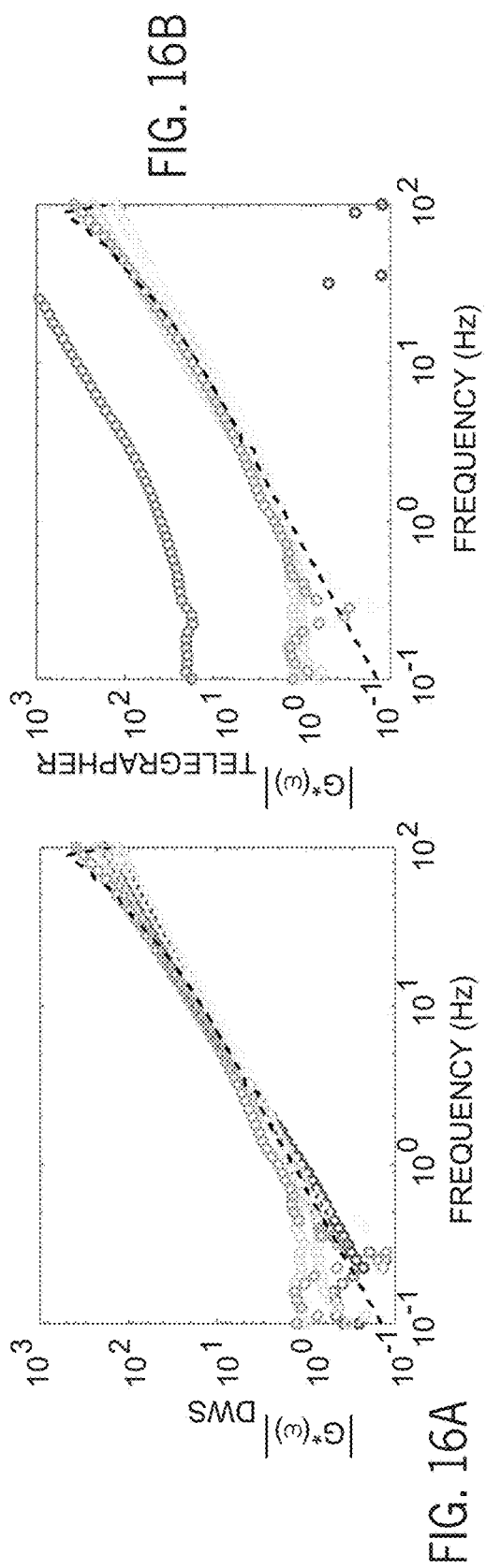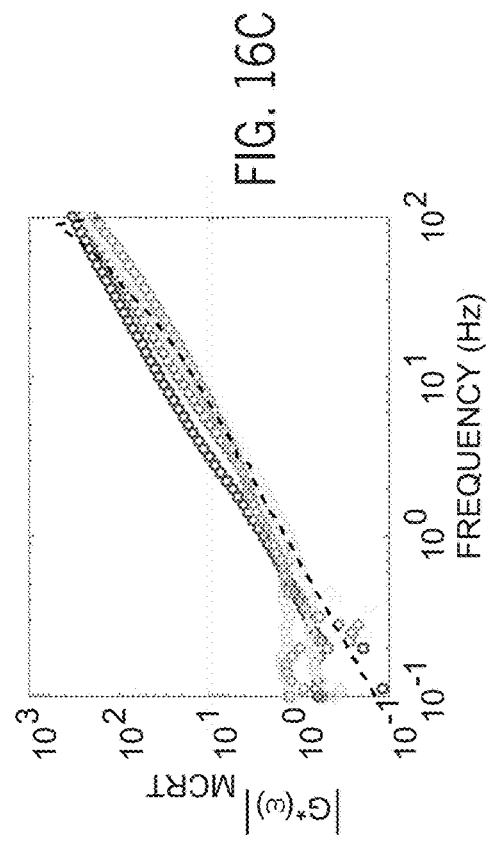

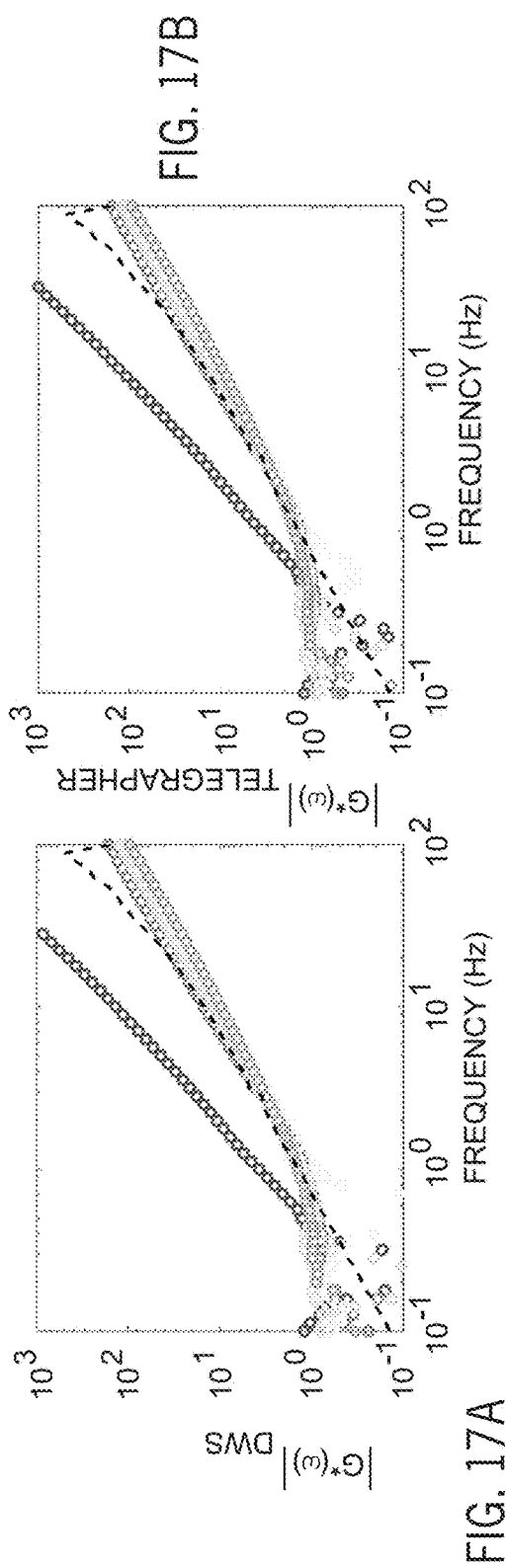

COMPENSATION FOR CAUSES OF TEMPORAL FLUCTUATIONS OF BACKSCATTERED SPECKLE PATTERNS IN LASER SPECKLE RHEOLOGY OF BIOLOGICAL FLUIDS

CROSS-REFERENCE TO RELATED APPLICATIONS

This application represents the national stage entry of PCT International Application No. PCT/US2013/059906 filed Sep. 16, 2013, which claims the benefit of U.S. Provisional Patent Application Ser. No. 61/701,819 filed Sep. 17, 2012 and 61/738,808 filed Dec. 18, 2012. The disclosures of both of the above-mentioned provisional applications is are incorporated herein by reference for all purposes.

STATEMENT REGARDING FEDERALLY SPONSORED RESEARCH OR DEVELOPMENT

This invention was made with government support under Grants Numbers R21 HL 088306, R21 HL 088306-02S1, and U54 EB 015408-01-8416 awarded by the NIH. The government has certain rights in the invention.

TECHNICAL FIELD

The present invention relates to optical systems and methods for the measurement and monitoring of the material properties of biological fluids and, in particular, to a means for compensation for multiple scattering and/or absorption in laser speckle rheology (LSR) of the biological fluids during such monitoring.

BACKGROUND

Typically, the progression of a disease in the biological tissue is accompanied by changes in tissue mechanical properties. Therefore, the availability of the modality effectuating the measurement of the mechanical properties of tissue in situ, in its native state, would provide critical diagnostic information.

Laser Speckle Rheology (LSR) is an optical approach that enables non-contact probing of tissue viscoelasticity. In LSR, tissue is illuminated by a mono-chromatic laser source and a high-speed CMOS camera is used to capture temporal intensity fluctuations of back-scattered laser speckle patterns. The temporal speckle intensity fluctuations are exquisitely sensitive to the displacements of light scattering centers undergoing Brownian motion, and the extent of this thermal motion reflects the viscoelastic properties of the surrounding medium. Speckle frames acquired by the high-speed camera are analyzed to obtain the speckle intensity temporal autocorrelation curve, $g_2(t)$. The $g_2(t)$ curve is a measure of the rate of temporal speckle intensity fluctuations and is closely related to the extent and time scales of particle motion, and in turn mechanical properties of the medium, defined by the viscoelastic modulus, $G^*(\omega)=G'(\omega)+iG''(\omega)$, which defines the mechanical behavior of materials. Traditionally, $G^*(\omega)$ is measured using a mechanical rheometer, by evaluating the ratio of an applied oscillatory stress to the corresponding induced strain in the specimen, over a limited oscillation frequency range. Using the LSR, the viscoelastic modulus, $G^*(\omega)$, can be assessed in a non-contact manner, by analyzing the $g_2(t)$ and retrieving displacement of scattering particles, often quantified by the mean square displacement (MSD), denoted as $<\Delta r^2(t)>$. The generalized Stokes-Einstein relation (GSER) is then used to extract the viscoelastic modulus, $G^*(\omega)$, from the measured MSD. For relatively soft materials, the Brownian movements of scattering particles are fast and MSD increases quickly with time, eliciting rapid speckle fluctuations. In contrast, for mechanically rigid materials, scattering particles exhibit confined motions around a fixed position, which lead to restrained growth of MSD and slow variation of speckle patterns.

The primary challenge in extracting the viscoelastic modulus of tissue from speckle frame series lies in assessing the MSD from the measured $g_2(t)$ curve(s), partly because the rate of temporal speckle fluctuations depends not only on the Brownian displacement of scattering centers but also on the optical properties of the tissue—such as absorption and scattering coefficients and scattering anisotropy factor ($\mu_a$, $\mu_s$, and g)—that determine the transport of light within the illuminated volume. Accordingly, in order to accurately measure sample mechanical properties using LSR, it is required to isolate the influence of optical absorption and scattering from the $g_2(t)$ measurements to accurately describe the MSD.

Traditionally, diffusing wave spectroscopy (DWS) formalism is used to describe the relationship between the measured $g_2(t)$ and MSD for strongly scattering media with negligible absorption. In such media, light transport is often assumed to be diffusive. The majority of biological fluids and tissue, however, exhibit considerable absorption ($\mu_a>0$), and highly anisotropic scattering (g~0.9), and back-scatter light rays with sub-diffusive characteristics. In this case, the simple DWS formalism is modified to incorporate the knowledge of optical properties of the tissue to better explain the relationship between $g_2(t)$ and MSD. To compensate for shortcomings of the DWS, which assumes diffusive light transport, an analytical solution termed the "telegrapher equation" has been proposed. The telegrapher approach shares the ease and simplicity of the DWS expression but aims to incorporate the attributes of strong absorption, scattering anisotropy, and non-diffusive propagation of rays within short source-detector distances in a modified photon-transport equation. Alternatively, a Monte-Carlo ray tracing (MCRT) algorithm may be used to simulate the propagation of light in a medium of known optical properties and derive a numerical solution for speckle intensity temporal autocorrelation curve as a function of particle Brownian displacement.

A new polarization-sensitive correlation transfer (PSCT)-MCRT algorithm was proposed for describing light propagation in purely scattering media and accounting for the fluctuations of scattered light (See Z. Hajjarian and S. K. Nadkarni, "Evaluation and Correction for Optical Scattering Variations in Laser Speckle Rheology of Biological Fluids," PLoS ONE 8, e65014, 2013). The performance of PSCT-MCRT in estimating the MSD of Brownian particles in purely scattering media showed improved accuracy of estimating sample mechanical properties compared to the DWS approach [3]. Most biological tissues, however, in addition have light absorbing characteristics that are typically not taken into account in devising the MSD.

Fluid Biological Tissues—biological fluids (also referred herein as biofluids)—such as cerebrospinal fluid (CSF) mucus, synovial fluid, and vitreous humorous function as shock-absorbents, allergen and bacteria trappers, and lubricants in different organs and organ systems. Biofluids have distinct rheological characteristics and exhibit both solid-like and fluid-like behavior over different loading conditions and size scales. As the evidence of correlation between viscoelastic properties of biofluids and initiation and progression of various bodily maladies becomes available, there arises a need in development of a methodology that would allow the user to evaluate mechanical properties of biological fluids in situ under native conditions to advance clinical disease diagnosis and treatment monitoring.

SUMMARY OF THE INVENTION

Embodiments of the invention provide a method for determining a viscoelastic modulus of an optically scattering tissue sample with the use of laser speckle rheology (LSR). The method comprises (i) acquiring, with an optical detector, data sets representing time evolution of speckle associated with the sample irradiated with light from a light source; (ii) determining an optical property of the optically scattering tissue sample based at least on a radial profile of flux determined from the acquired data sets; and (iii) calculating a mean square displacement (MSD) value based on intensity decorrelation function describing the time evolution of speckle based on the determined optical property.

Embodiments of the invention additionally provide a method for determining a viscoelastic modulus of an optically scattering biological fluid with the use of laser speckle rheology (LSR), which includes acquiring, with an optical detector, data sets representing time evolution of speckle associated with the biological fluid irradiated with laser light and calculating an intensity decorrelation function based on the acquired data sets. The method additionally includes determining parameters of a fitting curve, for the intensity decorrelation function, based on the Laplace transform of a momentum transfer distribution associated with photon scattering by the biological fluid and calculated based on at least a reduced scattering coefficient characterizing distribution of optical scatterers in the biological fluid. A method further includes deriving a value of the viscoelastic modulus based on a closed algebraic form of the fitting curve.

Embodiments of the invention further provide an article of manufacture including a computer program product that enables a computer processor to effectuate computational steps of the method of an embodiment of the invention. Embodiments of the invention further provide a measurement system including a system configured to perform laser speckle rheological measurements of a sample of optically scattering liquid and a computational sub-system adapted to perform calculations associated to an embodiment of the method of the invention.

BRIEF DESCRIPTION OF THE DRAWINGS

The invention will be more fully understood by referring to the following Detailed Description in conjunction with the Drawings, of which:

FIG. 15A: samples with higher $\mu'_s$ have a smaller $\mu_a$; FIG. 15B: $\mu'_s$ and $\mu_a$ proportional.

FIGS. 16A, 16B, 16C: Viscoelastic modulus, $|G^*(\omega)|$, derived from $g_2(t)$ curves of FIG. 15A, using the DWS equation, the Telegrapher equation, and the PSCT-MCRT algorithm, respectively, for glycerol suspensions of identical mechanical properties and varying $\mu'_s$ and $\mu_a$. The viscoelastic modulus measured using a conventional rheometer is shown as a black dashed curve. $|G^*(\omega)|$ derived from speckle fluctuations, using DWS equation exhibit an unexpected close agreement with conventional rheology even in the case of weak scattering and strong absorption. In contrast, telegrapher equation fails, whenever strong absorption accompanies highly anisotropic scattering. PSCT-MCRT agrees well with rheometry results in most cases, but slightly over-estimates the modulus in weakly scattering samples of strong absorption.

FIGS. 17A, 17B, 17C: Viscoelastic modulus, $|G^*(\omega)|$, obtained from $g_2(t)$ curves of FIG. 16B using the DWS equation, the Telegrapher equation, and the PSCT-MCRT, respectively. The viscoelastic modulus measured using a conventional rheometer is shown as a black dashed curve. DWS and telegrapher equations match the results of conventional rheometry for samples with non-negligible $\mu_a$. The PSCT-MCRT results are in close agreement with conventional rheology for any arbitrary set of optical properties.

DETAILED DESCRIPTION

Figure 1:
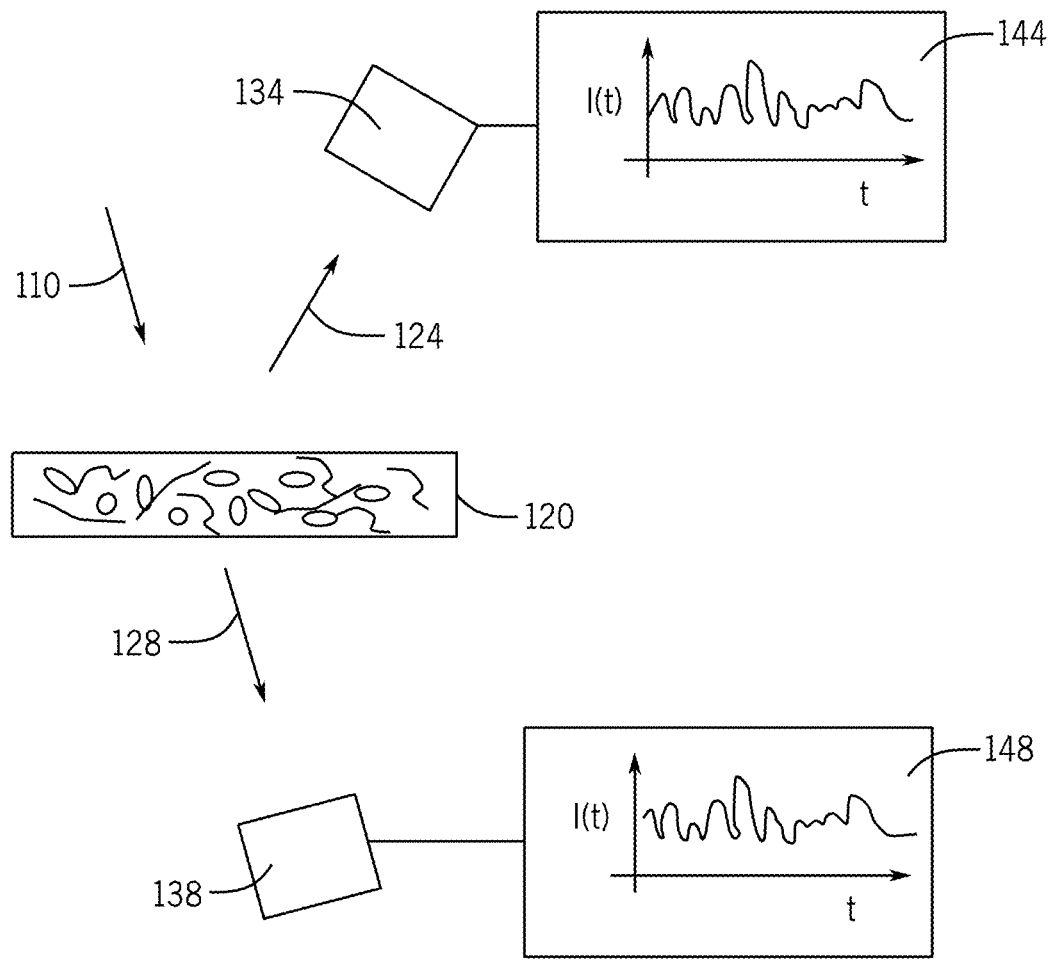
FIG. 1 is a diagram illustrating measurement of intensity fluctuations of light that has interacted with a biological fluid sample.

The idea of this invention addresses the role of optical absorption and/or scattering in modulating temporal speckle intensity fluctuations using test phantom samples that cover a wide range of optical properties pertinent to biological tissues. In accordance with embodiments of the present invention, the problem of non-invasive assessment of the viscoelastic modulus of a biological fluid having varying optical and mechanical characteristics is solved by devising an algorithm for extracting the data representing such modulus from the biological-fluid-related speckle fluctuation information (that has been obtained with the LSR-based measurements) while decoupling the contribution (to the LSR speckle fluctuation data) introduced by multiple scattering and/or absorption and displacement of particles of the biological fluid. In particular, the application of DWS, telegrapher, and PSCT-MCRT approaches in describing and correcting for the influence of varying absorption and scattering properties on the measured MSD from speckle intensity fluctuations are presented, and the accuracy of each of the three approaches in measuring the mechanical properties in phantom samples covering the range of optical properties relevant to tissue is assessed.

The presented empirical results suggest the prominent role of optical properties in modulating temporal speckle fluctuations and establish that the isolation and correction of optical properties is needed for precise interpretation of LSR measurements of the mechanical properties of a sample. It is shown that the PSCT-MCRT provides the most accurate estimation of sample viscoelastic properties via the MSD with samples possessing not only scattering characteristics but also absorption characteristics. The comparison among the different methods demonstrates that even for samples with non-negligible absorption. DWS exhibits accurate results and performs similarly to the PSCT-MCRT approach in its capability to measure MSD and retrieve the viscoelastic modulus. On the other hand, the telegrapher equation does not provide a significant improvement over DWS formalism and fails in the presence of strong absorption and anisotropic scattering. These findings provide a definitive affirmation that the LSR methodology can be used as a diagnostic tool for evaluating the mechanical properties of biological materials with any, substantially arbitrary, set of optical properties.

In related art, the mechanical behavior of a medium is sometimes described using the DLS approach with the purpose of demonstration that the mechanical properties of homogenous medium (such as complex fluids) can be examiner with the use of exogenous light scattering microparticles introduced to such medium. According to the DLS principle time-varying fluctuations of light intensity are measured at a single spot of the medium, and averaging over several cross-correlation functions that evolve in time is required to obtain the intensity correlation function, $g_2(t)$. Since in DLS $g_2(t)$ is measured over a single spot, the required data-acquisition time (on the order of several minutes to hours) is orders of magnitude larger than the typical time scale of laser-speckle intensity fluctuations, thereby attesting to impracticality of the use of the DLS for analysis of tissue in situ.

In contradistinction with the DLS, as previously demonstrated, the LSR successfully lends itself to the in situ analysis. See, for example, Characterization of atherosclerotic plaques by laser speckle imaging, Nadkarni et al., in *Circulation* 112: 885-892, 2005; Measurement of fibrous cap thickness in atherosclerotic plaques by spatiotemporal analysis of laser speckle images; Nadkarni et al., in *J. Biomed. Opt.* 11: 21006, 2006; Laser speckle imaging of atherosclerotic plaques through optical fiber bundles; Nadkarni et al., in *J. Biomed. Opt.* 13: 054016, 2008; Intravascular laser speckle imaging catheter for the mechanical evaluation of the arterial wall, Hajjarian et al., in. *J. Biomed. Opt.* 16: 026005, 2011; and Evaluating the viscoelastic properties of tissue from laser speckle fluctuations, Hajjarian et al., in *Sci. Rep.* 2: 316. However, the analysis of even a single $g_2(t)$ curve, obtained with the use of LSR, generates plethora of information representing various relaxation times, which complicates the examination of speckle dynamics and reduces the accuracy of results. According to embodiments of the invention, the LSR methodology is hereby extended with the use of an optical-scattering-and-absorption compensation algorithm to increase the accuracy of the assessment of mechanical properties of fluids or, in general, a material (such as a tissue, for example) that has a clearly recognized scattering and/or absorption characteristics. The proposed algorithm is adapted to process the LSR-measurement data representing viscoelastic moduli of either a liquid phantom or biological fluid the optical and/or mechanic properties of which can be, generally speaking, substantially arbitrary. In particular, embodiments of a polarization-sensitive correlation transfer Monte-Carlo ray tracing (PSCT-MCRT) algorithm, discussed in this disclosure, are used to assess the contribution of optical properties to evolution of the LSR-acquired speckle (in particular, speckle intensity fluctuation) for a chosen concentration of scatterers in a fluid of interest.

In particular, in order to measure accurately viscoelasticity of the biofluid using the LSR, the dependence of viscoelasticity on light scattering and/or absorption properties should be decoupled from that on the mechanical properties of the biofluid.

According to the idea of the invention, the accuracy of the LSR methodology in determination of the mechanical characteristics of biofluids is increased by compensating for variations of optical scattering and/or absorption characteristics in samples with varying optical and mechanical properties. To this end, optical properties of a sample are calculated from time-averaged speckle data, and a polarization sensitive correlation transfer Monte-Carlo ray tracing (PSCT-MCRT) algorithm is implemented to characterize and correct for the contribution of optical scattering in evaluation of MSD. Using this approach, complex viscoelastic moduli of test phantoms and biological fluid samples are evaluated and compared with reference-standard mechanical measurements obtained using a rheometer.

FIG. 1 shows a diagram schematically illustrating the principle of measurement of laser speckle intensity fluctuation caused by a sample. Depending on a particular configuration, incident polarized highly coherent light 110 is reflected by and/or transmitted through the sample 120 having numerous intrinsic light-scattering elements. Upon interaction with the sample 120, light is detected (in a reflection arm—as beam 124, and/or in a transmission arm—as beam 128) by an appropriate detector system (134, 138) to acquire image data representing image of laser speckle pattern produced by light scattered by the sample 120 as a function of time and to acquire and store, on tangible non-transient computer-readable medium, the acquired data. Such interferometric image data are further processed to determine detected light intensity fluctuations 144,148 associated with the illuminated sample 120.

Image Acquisition and Analysis

FIG. 2 provides an example of an embodiment 200 of the experimental set up configured to operate in reflection (backscattering regime). The embodiment 200 includes a laser source 210 (such as a He—Ne laser, with output of about 20-30 mW at 633 nm; JDSU 1145) producing light 110 that, upon passing through an optical train including a linear polarizer 214 and a beam expander (10:1) 218, was focused into an approximately 50 micron spot onto the biofluid sample 120 through an optical system 220 including a lens 222 and a beam splitter 224. In a related implementation, where the working distance between the lens 222 and the sample 120 is varied, depth-resolved mapping of the sample 120 can be realized. Optionally, light 110 was transmitted through a single-mode fiber (SMF) 226 prior to traversing the polarize 214. Time series of images of the sample 120 in light 228 backscattered by the sample 120 were acquired through a polarizer 230 (arranged in cross orientation with the polarizer 214, to reduce the unwanted acquisition of specularly reflected light) with a high-speed CMOS camera 232 (such as PixelLINK PL-761F, Ottawa. Canada) through a lens with adjustable focal length (such as, for example, a focusing lens system MLH-10x by Computar, Commack, N.Y.). The use of CMOS camera 232 to acquire laser speckle patterns from the sample 120 in a 180 degree backscattering geometry enhances the statistical accuracy in measuring $g_2(t)$ by simultaneous ensemble averaging of multiple speckle spots, which significantly reduces data acquisition time. The acquired imaging data were stored and processed with the use of a pre-programmed data-processing electronic circuitry (such as a computer processor) 236, and optionally displayed for visualization in a required format on a display (not shown). The acquisition of imaging data representing the sample 120 in backscattered light 228 was conducted at a predetermined rate (for phantom samples: at about 490 frames-per-second, fps, and for tissue samples: at about 840 fps to ensure that fast sample dynamics is appropriately detected) during the acquisition time periods of about 2 seconds. The acquired sequences of speckle patterns were optionally additionally processed to obtain temporally-averaged intensity (a diffuse reflectance profile) for ROI of about 296-by-296 pixels, which corresponded to the field-of-view (FOV) of about 1 mm². It is appreciated that an embodiment related to that of FIG. 2 can be adapted to operate in transmission (or forward scattering regime).

Figure 2A:
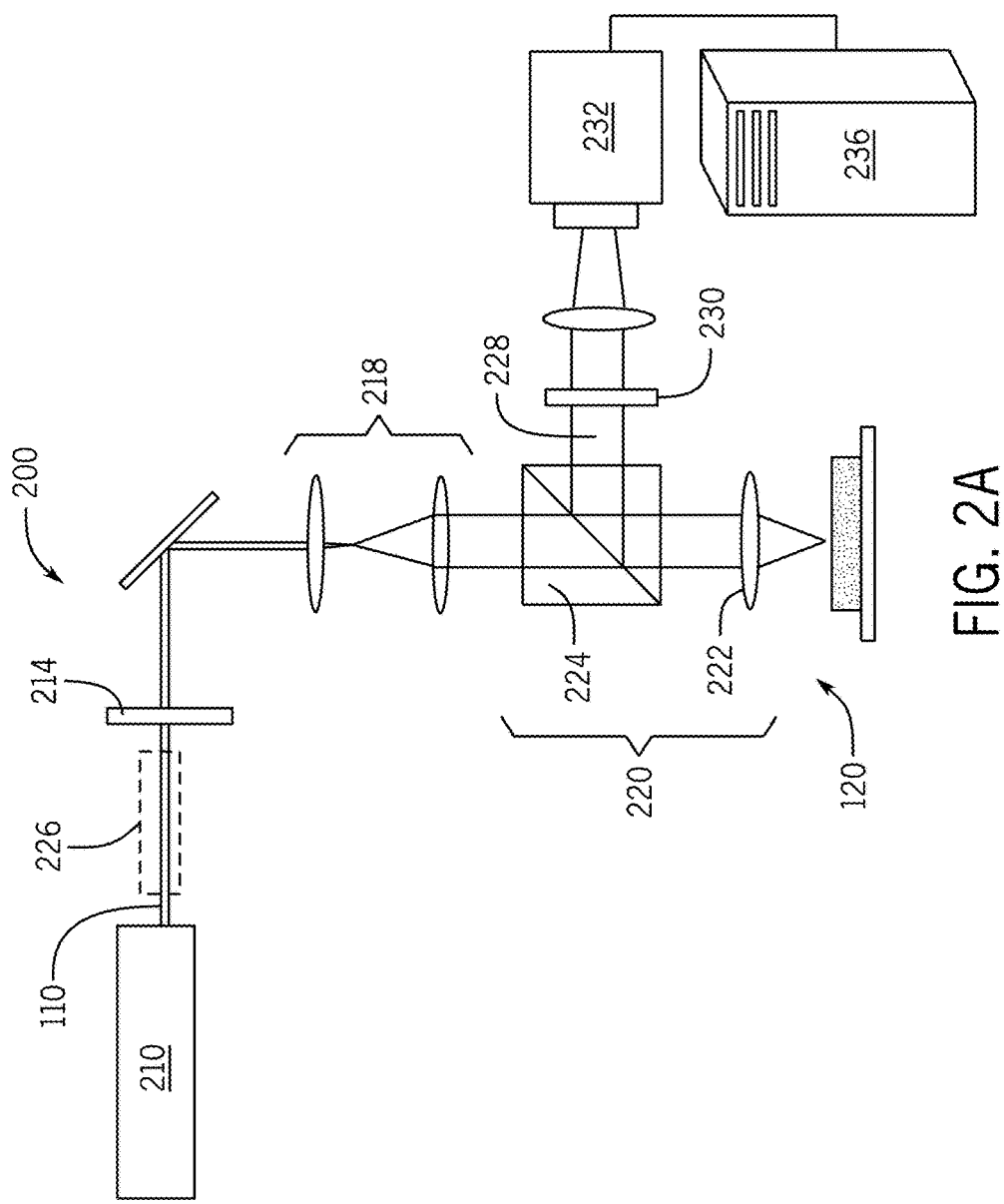
FIG. 2A is an embodiment of a laser-speckle-based imaging system configured to operate in a backscattering regime, in accord with an embodiment of the invention.
Figure 2B:
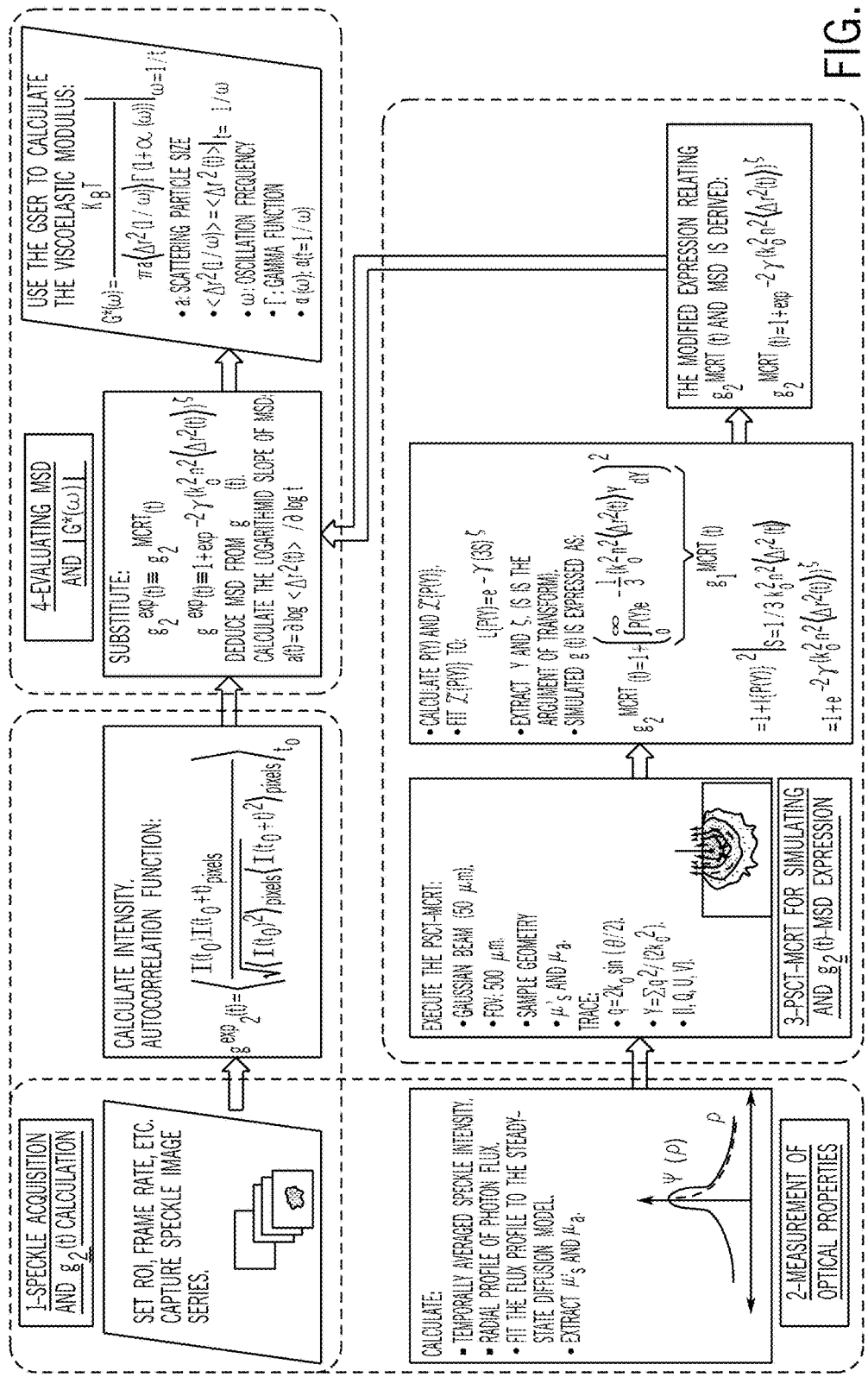
FIG. 2B is a block-scheme representing an embodiment of the PSCT-MCRT algorithm according to the invention.

Data representing the interaction of light with various media were acquired, with the use of the embodiments of LSR measurement set-up of FIG. 2A, in a form of series of speckle data frames and appropriately processed with the use of cross-correlation analysis of the first data frame with the subsequent frames, required spatial and temporal averaging (over multiple data points) for different phantom samples and biofluid samples. The speckle size-to-CCD pixel ratio was set to at least four to maintain sufficient spatial sampling and speckle contrast. The speckle intensity temporal autocorrelation curve, $g_2(t)$, was calculated by measuring the correlation between pixel intensities in the first speckle image and subsequent images. Spatial averaging was performed over the entire frame of pixels, the $g_2(t)$ curves evolving in time were averaged to enhance the accuracy of temporal statistics as follows;

$$g_2^{exp}(t) = \left\langle \frac{\langle I(t_0)I(t_0+t)\rangle_{pixels}}{\sqrt{\langle I(t_0)^2\rangle_{pixels}\langle I(t_0+t)^2\rangle_{pixels}}} \right\rangle_{t_0} \quad (1)$$

where $I(t_0)$ and $I(t+t_0)$ refer to the speckle intensity at times $t_0$ and $t+t_0$, and $<>_{pixels}$ and $<>_{t_0}$ indicate spatial and temporal averaging over all the pixels in the images and for entire imaging duration (for example ~2 sec), respectively.

MSD Evaluation with the Use of DLS and DWS Formalisms

For single or strong multiply-scattering media, DLS and DWS theories, respectively, have expressed the measured $g_2(t)$ (eqn. (1)) as a function of MSD as follows:

$$g_2^{DLS@180°}(t) = 1 + e^{-\frac{4}{3}k_0^2n^2\langle\Delta r^2(t)\rangle}, \text{ and} \quad (2)$$

$$g_2^{DWS@180°}(t) = 1 + e^{-2\gamma\sqrt{k_0^2n^2\langle\Delta r^2(t)\rangle}}. \quad (3)$$

Here $k_0$ is the wave number, n is the refractive index of the sample, and $\gamma$ is an experimental parameter that reflects the ratio of long diffuse path lengths to short non-diffusive ones. It is used to expand the theoretical limitations of DWS in back-scattering geometry and is generally assumed to be $\gamma=5/3$. The DLS formalism is not valid for the moderate to strongly scattering samples used in this work In a specific case, when the absorption properties of the biofluidic sample are taken into account, and based on the diffusion approximation, the relationship between $g_2(t)$ and MSD in the back-scattering geometry is as follows:

$$g_2^{DWS}(t) \sim e^{-2\gamma\sqrt{k_0^2n^2\langle\Delta r^2(t)\rangle+\frac{3\mu_a}{\mu_s'}}} \quad (4)$$

where $\mu'_s=\mu_s(1-g)$ is the reduced scattering coefficient. The second term in the exponents is related to optical properties of the sample and accounts for attenuation of long paths due to absorption. For strongly scattering media, this term reduces to zero (see Eq. (3)).

MSD Evaluation with the Use of the Telegrapher Formalism

The telegrapher equation, which is a modification of the DWS equation, results in the following final expression to describe the $g_2(t)$ and MSD relation (see, for example, P. A. Lemieux et al., "Diffusing-light spectroscopies beyond the diffusion limit: The role of ballistic transport and anisotropic scattering," Phys Rev E 57, 4498-4515 (1998):

$$g_2^{Tel}(x) = \left( \frac{1 + (D_0^2 - gz_e)x + (z_e - g)\sqrt{x(1+D_0^2 x)}}{\left(1 + (1-g)\sqrt{x(1+D_0^2 x)}\right)\left(1 + (D_0^2 + z_e^2)x + 2z_e\sqrt{x(1+D_0^2 x)}\right)} \right)^2 \quad (5)$$

Here, $D_0 = 1/3$ is the normalized photon diffusion coefficient, and $z_e = 2/3$ is related to boundary conditions and sample wall reflectivity, $x = k_0^2 n^2 \langle \Delta r^2(t) \rangle + 3\mu_a/\mu'_s$ and is the same as the argument in the exponent of Eq. (4), and g refers to the scattering anisotropy parameter. The telegrapher equation models the scattering anisotropy by introducing a void in the concentration of diffused photons at the vicinity of the light source, to emulate the impact of forwardly directed anisotropic scattering on the photon concentration profile. Moreover, this equation provides a distinct treatment of photon migration at different length scales, and provides an alternative closed-form solution to derive the MSD from the $g_2(t)$ curve in both transmission and back-scattering geometries for turbid media with strong absorption properties and anisotropic scattering.

MSD Evaluation with the Use of PSCT-MCRT Algorithm

An embodiment of the PSCT-MCRT algorithm according to the invention (FIG. 2B, Box 3) was employed to simulate $g_2^{MCRT}(t)$ curves and to derive a modified relationship between MSD and $g_2(t)$, for samples with arbitrary optical properties. The PSCT-MCRT model incorporated all experimental LSR parameters, for a focused Gaussian beam (50 µm) illuminating the sample placed in a cuvette (10 mm light path, 1.5 ml) with $\mu_a$ and $\mu'_s$, measured as above. A total of $10^5$ photons were tracked from the source to the receiver (FOV of 2 mm). The temporal speckle fluctuations were modified by the polarization state of detected light. As a result, the embodiment of the PSCT-MCRT algorithm incorporated attributes of the polarization state by tracking the Stokes' vector, [I Q U V], with respect to the corresponding reference frame. Euler equations were used to modify the Stokes' vector upon scattering and transport within the medium. At the receiver site, a final rotation was applied (with the polarizer P2) to redefine the Stokes' vector in the receiver coordinates system and since LSR setup captured the rapidly evolving speckle pattern of the cross-polarized channel, only the cross-polarized component of intensity was retained. To account for the momentum transfer (causing Doppler shift) at each scattering event, the scattering wave vector $q = 2k_0 \sin(\theta/2)$ was tracked, as well. Here $\theta$ is the polar angle of scattering. The total momentum transfer, defined as $Y = \Sigma q^2/(2k_0^2)$, with the summation over all scattering events involved in that path, represented the reduction of speckle intensity temporal autocorrelation due to all scattering events involved in each path. Consequently, $g_2^{MCRT}(t)$ was obtained by integrating the field temporal autocorrelation curves of all received rays, weighted by the corresponding momentum transfer distribution, P(Y), as:

$$g_2^{MCRT}(t) = \quad (5A)$$
$$1 + \left( \int_0^\infty P(Y) e^{-\frac{1}{3}k_0^2 n^2 Y \langle \Delta r^2(t) \rangle} dY \right)^2 = 1 + L\{P(Y)\}^2 \big|_{S=\frac{1}{3}k_0^2 n^2 Y \langle \Delta r^2(t) \rangle}.$$

From Eq. (5), it is noted that the term in brackets is simply the Laplace transform of P(Y), L{P(Y)} evaluated at $1/3 k_0^2 n^2 \langle \Delta r^2(t) \rangle$. L{(P(Y))} is equivalent to speckle field autocorrelation, $g_1^{MCRT}(t)$, in turn related to speckle intensity autocorrelation curve, $g_2^{MCRT}(t)$, through the Siegert relation as: $g_2(t) = 1 + |g_1(t)|^2$. PSCT-MCRT only provided the statistical histogram of photons' P(Y) and generated a numerical solution for L{P(Y)} (= $g_1^{MCRT}(t)$), and consequently $g_2^{MCRT}(t)$. To simplify Eq. (5), a parametric function was fitted to L{P(Y)} as follows:

$$L\{P(Y)\} = e^{-\gamma(3S)^\zeta}, \quad (6)$$

where S was the argument of the transform (complex frequency). The parameters $\gamma$ and $\zeta$ were derived from PSCT-MCRT simulation by numerical calculation of the total momentum transfer distribution P(Y), based on the experimentally evaluated values for $\mu_a$ and $\mu'_s$ and Mie theory calculations of g for each individual sample. Consequently, the following expression was derived for $g_2^{MCRT}(t)$ as a function of MSD:

$$g_2^{MCRT}(t) = 1 + e^{-2\gamma(k_0^2 n^2 \langle \Delta r^2(t) \rangle)^\zeta}. \quad (7)$$

The account for light propagation in turbid tissue, expressed as Eq. (7), provides an alternative numerical approach to describe the $g_2(t)$ and MSD relationship and implements a polarization-sensitive correlation transfer PSCT-MCRT algorithm. The PSCT-MCRT approach incorporates parameters of the illumination and collection setup, sample geometry and optical properties ($\mu_a$, $\mu_s$, g) to track the scattering wave vector, defined as $q = 2k_0 \sin(\theta/2)$, at each photon-particle collision event. The total momentum transfer of each photon (light path), $Y = \Sigma q^2/(2k_0^2)$, provides a superior description of correlation decay induced by all scattering events involved in each path. For a fixed choice of illumination/collection setup and sample geometry, the parameters $\gamma$ and $\zeta$ in Eq. (7) depend only on the optical properties, namely $\mu_a$ and $\mu'_s = \mu_s(1-g)$.

As discussed below, the MSD was derived from speckle intensity fluctuations using each of the three approaches (DWS, telegrapher, and PSCT-MCRT) and compared by substituting $g_2(t)$ in the corresponding equations with the experimentally values $g_2^{exp}(t)$ of Eq. (1) measured based on the time-varying laser speckle patterns. Finally, $|G^*(\omega)|$ was derived by substituting the derived MSD values in the generalized Stokes-Einstein relation (GSER) as $$G*(\omega) = \frac{K_B T}{\pi a \langle \Delta r^2(t) \rangle \Gamma(1 + \alpha(t))} \big|_{t=1/\omega} \quad (8)$$

Here $K_B$ is the Boltzman constant ($1.38 \times 10^{-23}$), T=297 (room temperature) is the absolute temperature (degrees Kelvin), a is the scattering/absorbing particle's radius (in nm, based on product specifications), $\omega = 1/t$ is the loading frequency, $\Gamma$ represents the gamma function, and $\alpha(t) = \partial \log \langle \Delta r^2(t) \rangle / \partial \log t$ corresponds to the logarithmic derivative of MSD.

Example 1

Influence of Optical Scattering on LSR Measurements

Aqueous glycerol mixtures with different glycerol-biofluid ratios were prepared to test the applicability of the LSR methodology to evaluating of the viscoelastic properties of liquid samples.

Particles of TiO2 (in the form of Anatase powder, diameter of about 400 nm, by Acros Organics, Geel, Belgium) were added to the mixtures in various concentrations (from about 0.04% to about 2% of volume fractions, corresponding to experimentally evaluated reduced scattering coefficients, $\mu'_s$: 1.3-84.8 mm$^{-1}$; total of N=18 different concentrations). The correspondence between the volume fractions (VF) of TiO2 particles and reduced scattering coefficients in summarized in Tables 1A, 1B, which is applicable to the FIGS. (7A and 7B) referred to below in Example 1 and related portions of the discussion:

TABLE 1A

| VF, % | 0.04 | 0.06 | 0.08 | 0.1 | 0.15 | 0.2 | 0.25 | 0.3 | 0.35 |
|---|---|---|---|---|---|---|---|---|---|
| $\mu'_s$, mm−1 (experimental) | 1.3 | 2.1 | 3.0 | 3.7 | 5.8 | 6.7 | 9.4 | 11.4 | 12.4 |
| $\mu'_s$, mm−1 (Theoretical) | 1.4 | 2.1 | 2.8 | 3.5 | 5.2 | 6.9 | 8.7 | 10.45 | 12.2 |

TABLE 1B

| VF, % | 0.4 | 0.45 | 0.5 | 0.6 | 0.7 | 0.8 | 0.9 | 1.0 | 2.0 |
|---|---|---|---|---|---|---|---|---|---|
| $\mu'_s$, mm−1 (experimental) | 14 | 16.4 | 15 | 18 | 20.7 | 23.2 | 23.5 | 27.4 | 84.8 |
| $\mu'_s$, mm−1 (Theoretical) | 13.9 | 15.6 | 17.4 | 20.9 | 24.4 | 27.9 | 31.4 | 34.8 | 69.7 |

Figure 3:
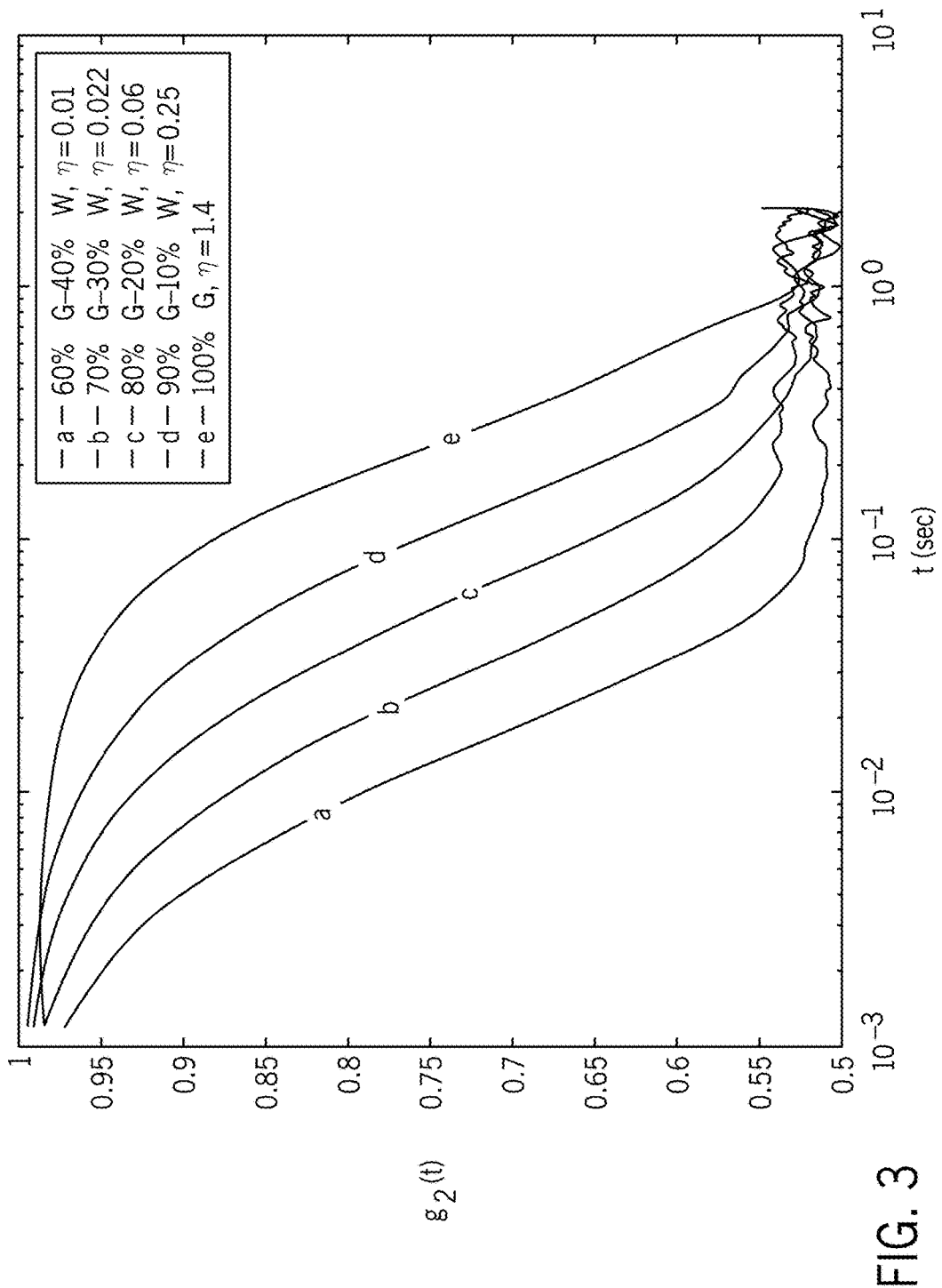
FIG. 3 is a plot presenting decorrelation curves, for aqueous glycerol mixtures of different viscosities and containing a small percentage of light-scattering particles, obtained with the use of an embodiment of the invention.

The resulting solutions were vortexed extensively to assure that scattering particles were totally disintegrated and evenly disseminated throughout the solutions. About 1.5 ml of a so prepared liquid sample were placed in a sealed spectroscopic couvette for the LSR measurements and about 2 ml were used to fill the gap of a parallel plate stainless steel geometry of 40 mm diameter for a conventional mechanical rheology testing. In this Example 1, the extrinsically added TiO$_2$ particles were utilized purely for the purpose of validating our approach over a large range of optical scattering concentrations relevant to the tissue sample FIG. 3 is a plot showing an intensity decorrelation function, $g_2(t)$, for aqueous glycerol mixtures of various concentrations (defined as 60% glycerol-40% water, 70%-30%, 80%-20%, 90%-10%, and 100%, respectively) with mixed in TiO$_2$ scattering particles (of about 400 nm in diameter) mixed in the amount of about 0.1 weight-%. Values of viscosity (in units of [η]=Pa S), corresponding to each of the measured mixtures, are also indicated. Due to similar optical properties of the samples of FIG. 3, the direct comparison of speckle dynamics is possible, which enables the relative assessment of viscosity values. As shown, a $g_2(t)$ curves corresponding to a liquid with higher viscosity decays slower than a $g_2(t)$ curve corresponding to a liquid of the same nature but of lower viscosity.

Figure 4:
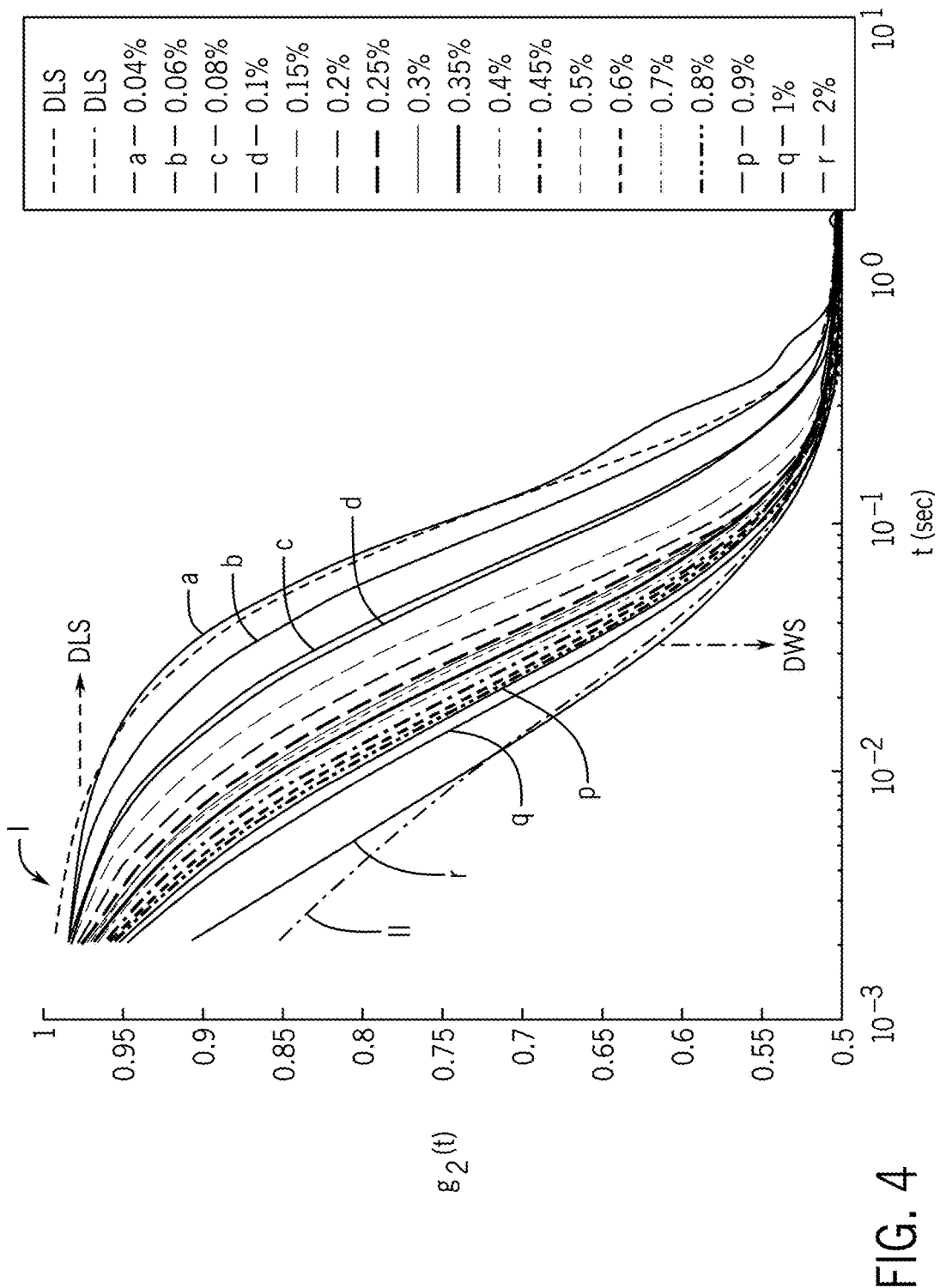
FIG. 4 is a plot presenting decorrelation curves, for an aqueous glycerol mixture containing light scattering particles in different concentrations, obtained with the use of an embodiment of the invention.

However, the variation in concentrations of scattering particles in the fluids of the same nature is expected to modify speckle dynamics, regardless of viscoelastic properties of the fluids. To illustrate this fact, FIG. 4 shows a plot with $g_2(t)$ curves calculated based on empirically acquired speckle data for phantom solutions containing 90% glycerol and 10% water (volume fraction), to which with TiO$_2$ particles were mixed in different concentrations. The TiO$_2$ concentrations, represented by N=18 samples, ranged from about 0.04% (labeled as "a") to about 0.06% (labeled as "b") and so on, to about 1% (labeled as "q"), to about 2% (labeled as "r"). Also displayed in FIG. 4, for comparison with the empirical results, are the theoretical curves I and II for $g_2(t)$ obtained according to the DLS and DWS methodologies, respectively, under the assumption of a radius of 0.3 μm for a TiO$_2$ particle. For this purpose, the theoretical particle diffusion constant of the corresponding glycerol solution was used in equations for DLS and DSW. Based on direct comparison of the curves a, b, . . . , p, q, and r with the curves I, II it is evident that speckle dynamics of the above-defined glycerol-water-TiO$_2$ mixes deviate from predictions of DLS and DWS methodologies. The decorrelation curves fall somewhere between the DLS and DWS curves for most of the values of concentration of scattering particles. Put differently, by changing the TiO$_2$ concentration in the glycerol/water mix from 0.04% to 2%, $g_2(t)$ curves sweep the gap of operational values between the two theoretical limits, thereby demonstrating a dramatic change in speckle fluctuation rate. Consequently, while viscosities of all phantom samples used for the purposes of FIG. 4 are substantially the same, large deviation is observed in speckle dynamics. A skilled artisan would readily conclude that the use of either of the DLS and DWS formalisms for interpreting speckle dynamics and extracting mean square displacements (MSD) of scattering particles is improper as such used results in erroneous estimation of a decorrelation curve and a corresponding complex viscoelastic modulus.

Figure 5:
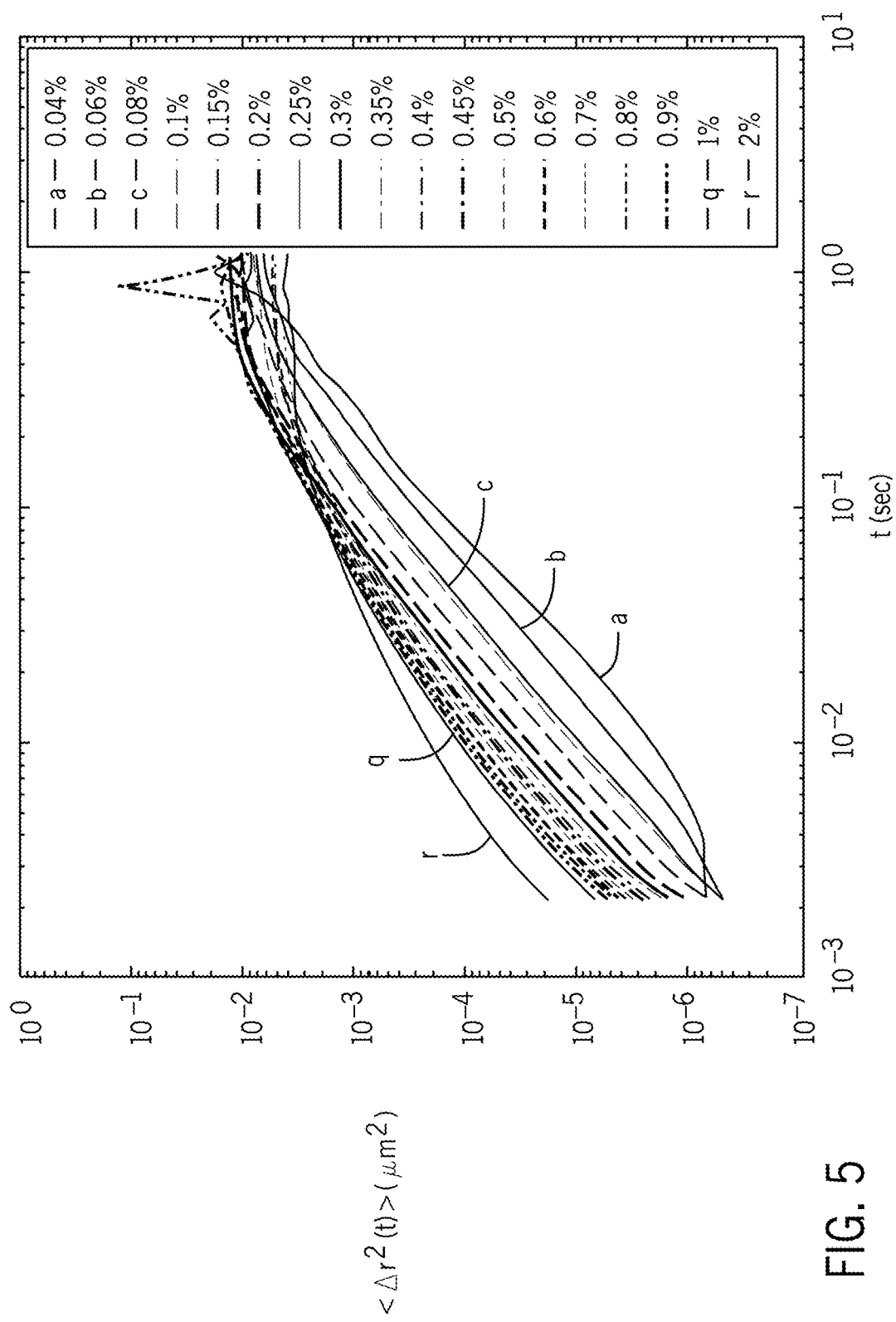
FIG. 5 is a plot presenting raw MSD-values for light-scattering particles in mixtures of FIG. 4 under the assumption of diffusion approximation.

FIG. 5 is a plot demonstrating the MSD values for TiO$_2$ scattering particles estimated based on respectively-corresponding $g_2(t)$ curves of FIG. 4 with the use of the DWS formalism for backscattering geometry. Such formalism is discussed, for example, by Cardinaux F. et al. (in Microrheology of Giant-Micelle Solutions, *Europhysics Letters* 57: 7, 2002). In deriving the results presented in FIG. 5, it was assumed that the diffusion approximation was valid for all considered concentrations of scattering particles. A large variation is observed among the curves of FIG. 5, which supports the conclusion that if raw MSD curves are not compensated for variations in optical properties, the complex viscoelastic modulus derived in reliance on such data will be biased due to variations in scattering concentrations.

When performing the measurements with a conventional mechanical rheometer, the AR-G2 rheometer (TA Instruments, New Castle, Del.) was used. A 40 mm diameter stainless steel parallel plate geometry was employed and the frequency sweep oscillation procedure was carried out to evaluate G', G", and G* over the frequency range from about 0.1 Hz to about 100 Hz. For aqueous glycerol mixtures, such tests were carried out in the room temperature, 25° C., and the strain percentage was controlled to be 2% thorough the procedure. (Similar procedures were performed on synovial fluid and vitreous humorous, as discussed below, except that the strain percentage was set to about 1% and the synovial fluid samples were evaluated at about 37° C.)

Figure 6:
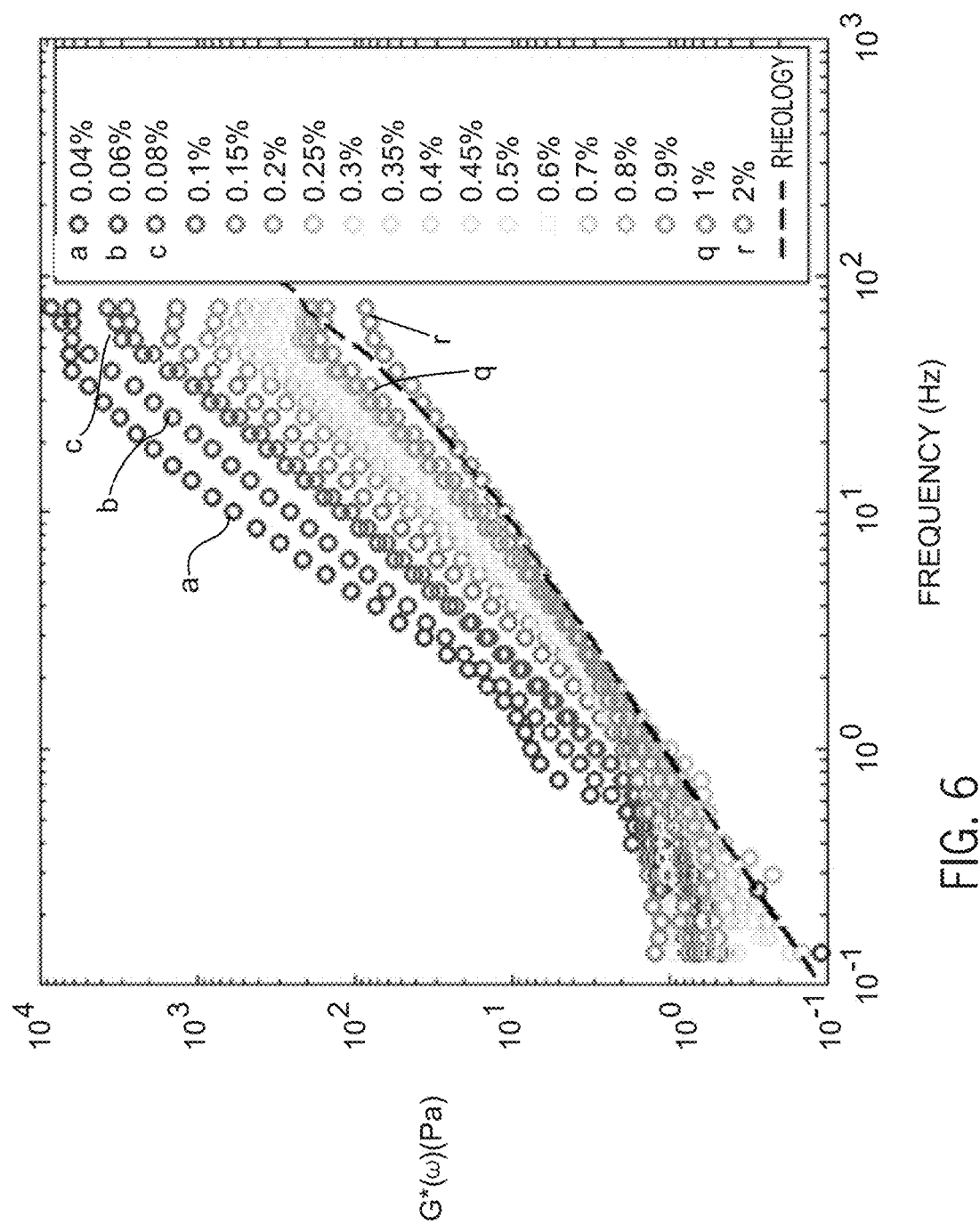
FIG. 6 is a plot presenting raw, uncorrected data for viscoelastic moduli for the mixtures of FIG. 4, calculates with the use of generalized Stokes-Einstein equation from the MSD values of FIG. 5.

FIG. 6 is a plot presenting the estimated frequency-dependent complex viscoelastic modulus, G*(w), calculated by substituting the raw MSD curves of FIG. 5 in the generalized Stokes Einstein Eq. (8).

A person of skill in the art would appreciate that G*(ω) data of FIG. 6 calculated from raw MSD values do not match the results of conventional mechanical testing (as shown by most of the curves in FIG. 6). In particular, G*(ω) is overestimated, especially at lower concentrations of scattering particles due to slower decorrelation of speckle intensity. From the presented results it appears that is only at $TiO_2$ concentration of about 2% (sample q) that strong multiple scattering dominates, and the values of G*(ω) substantially converge to the results obtained with mechanical rheometry. It may be concluded, therefore, that, while for a substantially optically dense phantom sample the diffusion theory may be used to model transport of photons and account for correlation transfer of the received light, such theory is substantially improper for the enablement of accurate estimation of G*(ω) of samples of arbitrary optical properties. Accordingly, the accurate determination of G*(ω) requires the use of an alternative model of light propagation and correlation transfer.

Unlike the DLS and DWS methodologies, which measure temporal statistical parameters associated with intensity of light scatted by tracer particles of known sizes and concentrations, the LSR evaluates speckle fluctuations originated from specimens of arbitrary and a priori unknown optical properties. Therefore, the simplifying assumptions of diffusion approximation, and central limit theorem are not applicable for analysis of the LSR measurements and speckle dynamics critically depend on optical properties of the sample (such as, for example, absorption and scattering coefficients and asymmetry parameter ($\mu_a$, $\mu_s$, g), the latter defining transport of light in the medium)s. The calculation of $g_2(t)$ curves of phantom samples, displayed in FIGS. 3 and 4, substantiates that impetuous use of the diffusion approximation for extracting the MSD data from the $g_2(t)$ data leads to underestimation of MSD, as illustrated in FIG. 5. Consequently, the resulting G*(ω) values are erroneously biased by concentrations of scattering particles (FIG. 6).

The diffusion approximation describes transport of light for samples characterized by strong multiple scattering and minimal absorption. The above results indicate that the DWS formalism leads to inaccurate estimation of both the MSD and complex viscoelastic moduli for samples with optical scattering properties of intermediate (no too weak and not too significant) strength.

Example 1

Correction for Optical Scattering Variations in LSR According to the PSCT-MCRT Embodiment of Invention Since obtaining an analytical closed form for $g_2(t)$ (as a function of optical and mechanical properties of a medium) is not trivial, a parametric model is developed to correct for the effects of optical scattering in determining the MSD from $g_2(t)$ and to extract the complex viscoelastic modulus, as outlined in a flow-chart of FIG. 2a, for arbitrary concentration of optical scatterers in the biofluidic sample.

In one implementation, flux measurements were performed over an extended region of interest (ROI) of the sample 120 of FIG. 1 to evaluate the optical diffusion constant and the effective scattering coefficient and to determine absorption and scattering coefficients. In estimating optical properties from speckle frame series, a larger ROI is considered and pixels close to illumination center (a point in an image space representing a point at which the focused beam 110 is incident onto the sample 120) were abandoned.

Figure 7A:
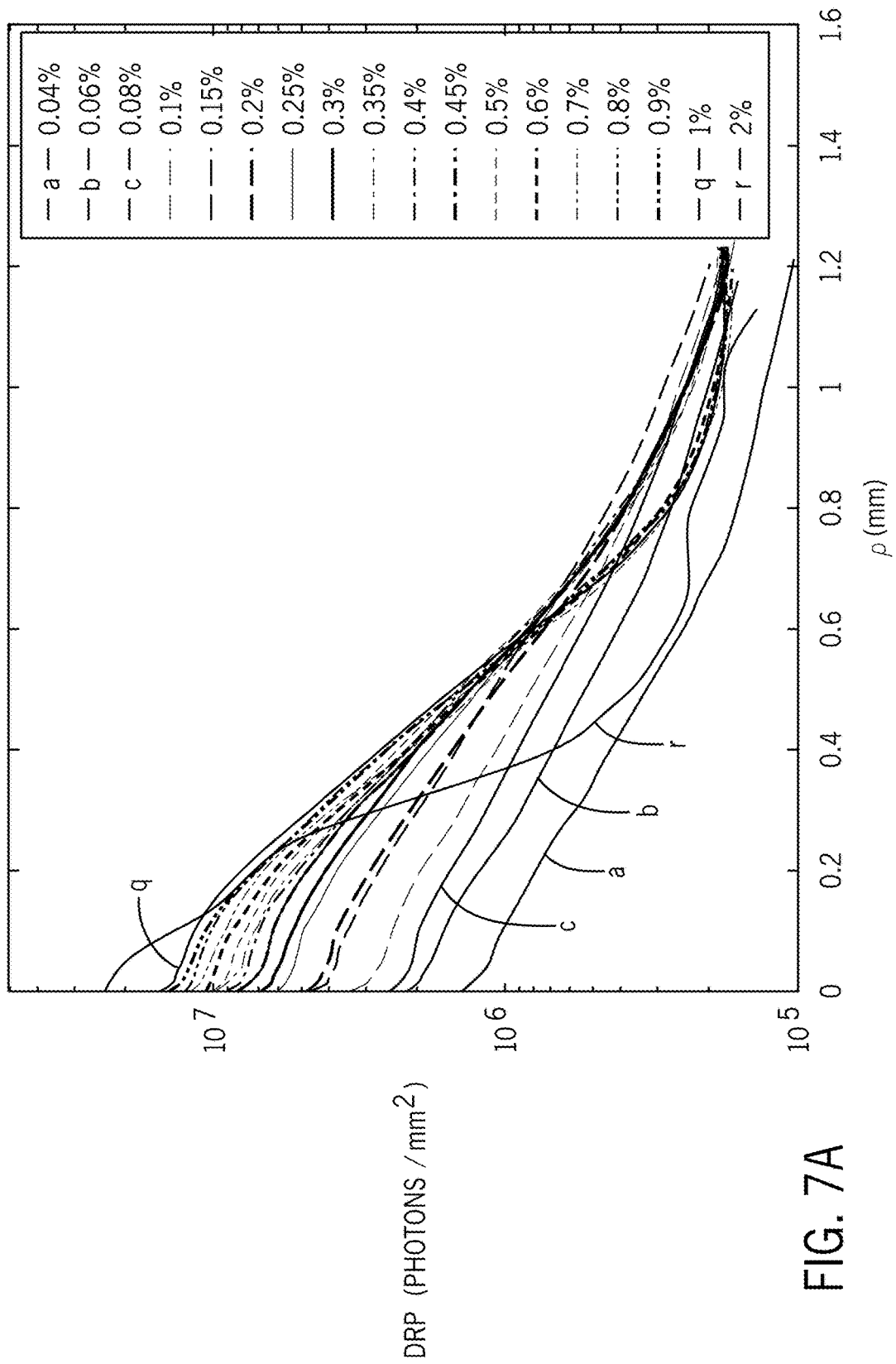
FIG. 7A is a plot presenting the radial flux profiles for the samples of FIG. 4.
Figure 7B:
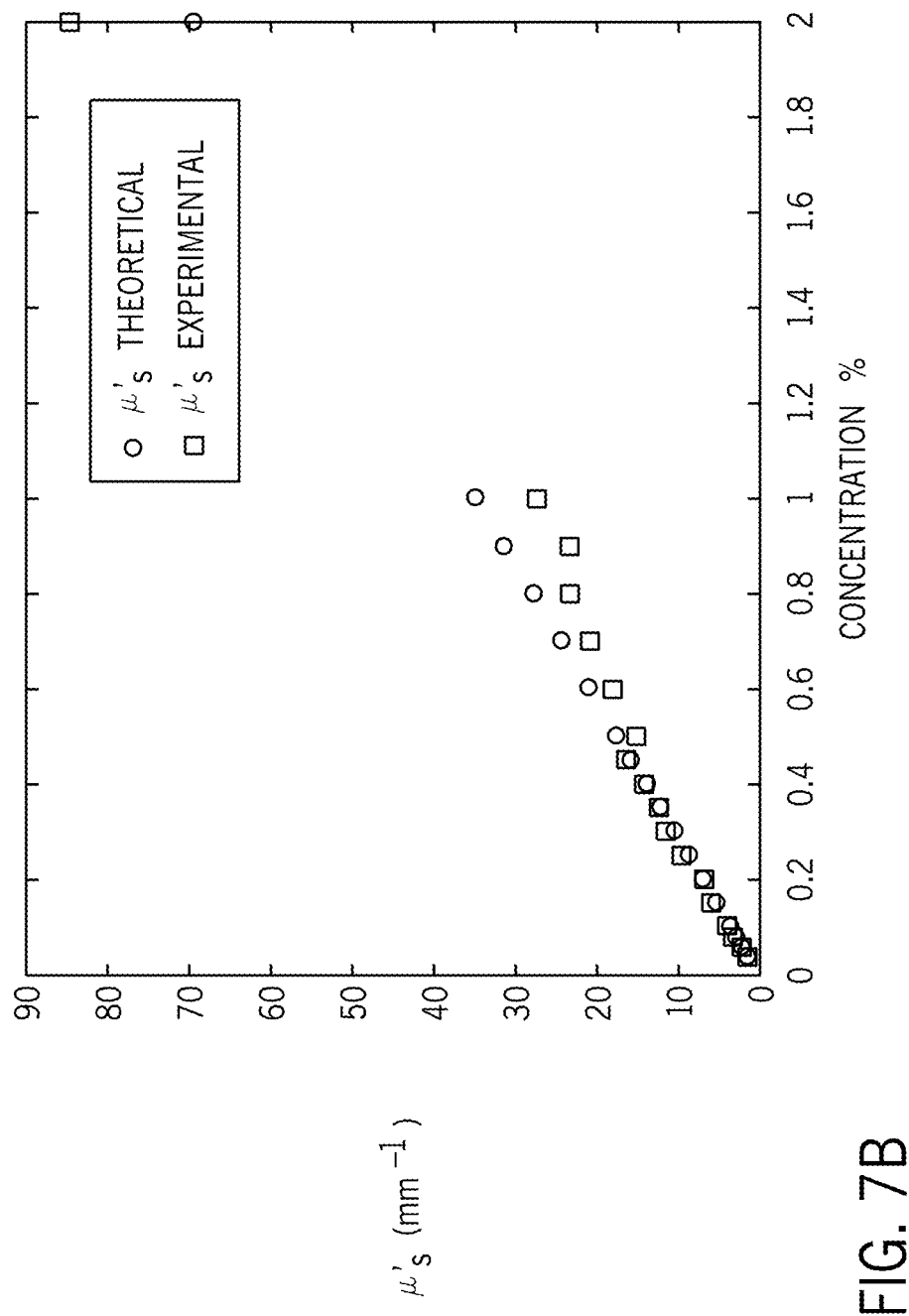
FIG. 7B is a plot presenting the results of theoretical and empirical determination for the reduced scattering coefficient according to an embodiment of the invention.

FIGS. 7A and 7B demonstrate the validity of an embodiment of the invention for evaluating the optical properties of phantom glycerol samples from time-averaged speckle images. The diffuse light remittance profile (DRP) curves are shown in FIG. 7A for the fluid samples discussed in reference to FIG. 4, and are in partial agreement with the predictions of diffusion theory, especially further away the illumination center. In FIG. 7A, a distance from the illumination center is denoted as ρ. The diffusion approximation is substantially improper for processing speckle dynamics and second order intensity statistics, due to smaller ROI of speckle dynamics acquisition, high frame rate (i.e. small exposure time), and a need to account for pixels close to illumination center (due to higher signal-to-noise ratio and contrast associated with such pixels). In FIG. 7A the number of remitted photons per unit area (photon flux) intensified at higher concentration and the inset of curves increased while slope of the photon flux profile became steeper.

Absorption and reduced scattering coefficients ($\mu_a$, $\mu'_s = \mu_s \times (1-g)$), the latter plotted in FIG. 7B, are evaluated from the photon flux profile of FIG. 7A obtained from temporally averaged speckle image series. Here, to assess the optical properties of a chosen medium, the data of FIG. 7A were processed to determine the radial profile of photon current (or flux based on camera responsivity (of about 28.1 DN/(nJ/cm²)) and photon energy (E=hv, h=Plank's constant, v=optical frequency). Accordingly, each digital number (which relates to a value representing intensity registered by a single pixel of the camera) corresponded to ~1 million photon per mm². This number was further corrected by taking into account the contributions of camera gain (of about 12.04 dB) and exposure time. The radial profile of flux was then fitted to the diffusion theory model assuming an isotropic point source located at a position (0, $z_0$) in an infinite medium and cylindrical coordinates:

$$\psi(\rho, z_0) = \frac{1}{4\pi D} \frac{e^{-\mu_{eff} r_1}}{r_1} \quad (9)$$

where $D = (3[\mu_a + (1-g)\mu_s])^{-1}$ is the photon diffusion constant, $\mu_{eff} = \sqrt{(3\mu_a [\mu_a + (1-g)\mu_s])}$ is the effective attenuation coefficient, and $r_1 = [(z-z_0)^2 + \rho^2]^{1/2}$, where $z_0 \sim l^*$, which is the reduced scattering coefficient). As a result, for each medium sample, the values of $\mu_a$ and $\mu_s'$ were determined.

The reduced scattering coefficient, $\mu'_s$, measured using this method is in close agreement with theoretical calculations particularly at low and intermediate scattering concentrations (See tables 1A and 1B). Deviations at higher concentrations were likely caused by clumping (larger particles, larger g) and sedimentation of $TiO_2$ particles (given the density of 4.23 g/cm³ for $TiO_2$ relative to <126 g/cm³ for glycerol mixture) which often resulted in lower $\mu'_s$ compared to Mie predictions. Moreover, at higher $TiO_2$ concentrations close proximity of adjacent particles could also lead to interactions of near-field radiation and reduce the backscattering efficiency, which influenced the measured $\mu'_s$ values.

For predominantly scattering samples, used in this Example 1, results were solely focused on the influence of $\mu'_s$ variations on the speckle dynamics and the role of absorption was not studied. (It is appreciated, nonetheless, that optical absorption is expected to eliminate rays with longest optical paths, corresponding to a large number of scattering events, and decelerate $g_2(t)$ curves). In the received back-scattered signal, attributes of scattering angular distribution were extensively washed off by multiple scattering. As a result, experimental evaluation of phase function and g was not trivial and instead theoretical Mie calculations were used to predict these parameters which resulted in g=0.6 for $TiO_2$ particles suspended in glycerol suspensions. Thus, in the current study, the effect of scattering anisotropy was not addressed in experiments. The resulting radial profiles of flux and assessed optical properties (specifically, scattering coefficients depicted in FIG. 7B) reveal close agreement (R=0.96, p<0.0001) with theoretical calculations, especially at lower concentrations of scattering particles. At higher concentrations of scattering particles, the experimentally estimated reduced scattering coefficient appears to deviate from the theoretically determined one, which is explained by imperfections of an experimental set-up. For example, clamping of particles and sedimentation give rise to lower values of empirically-determined reduced scattering coefficient. Moreover, limited dynamic range of CMOS camera (59 dB) somewhat distort photon current profile at high concentrations. According to Brown (Dynamic light scattering: the method and some applications, Oxford: Clarendon Press. xvi, 735 p.p, 1993), it is likely that the inter-particle structure and interaction are also partly responsible to erroneous estimation of scattering mean free path.

Figure 8A:
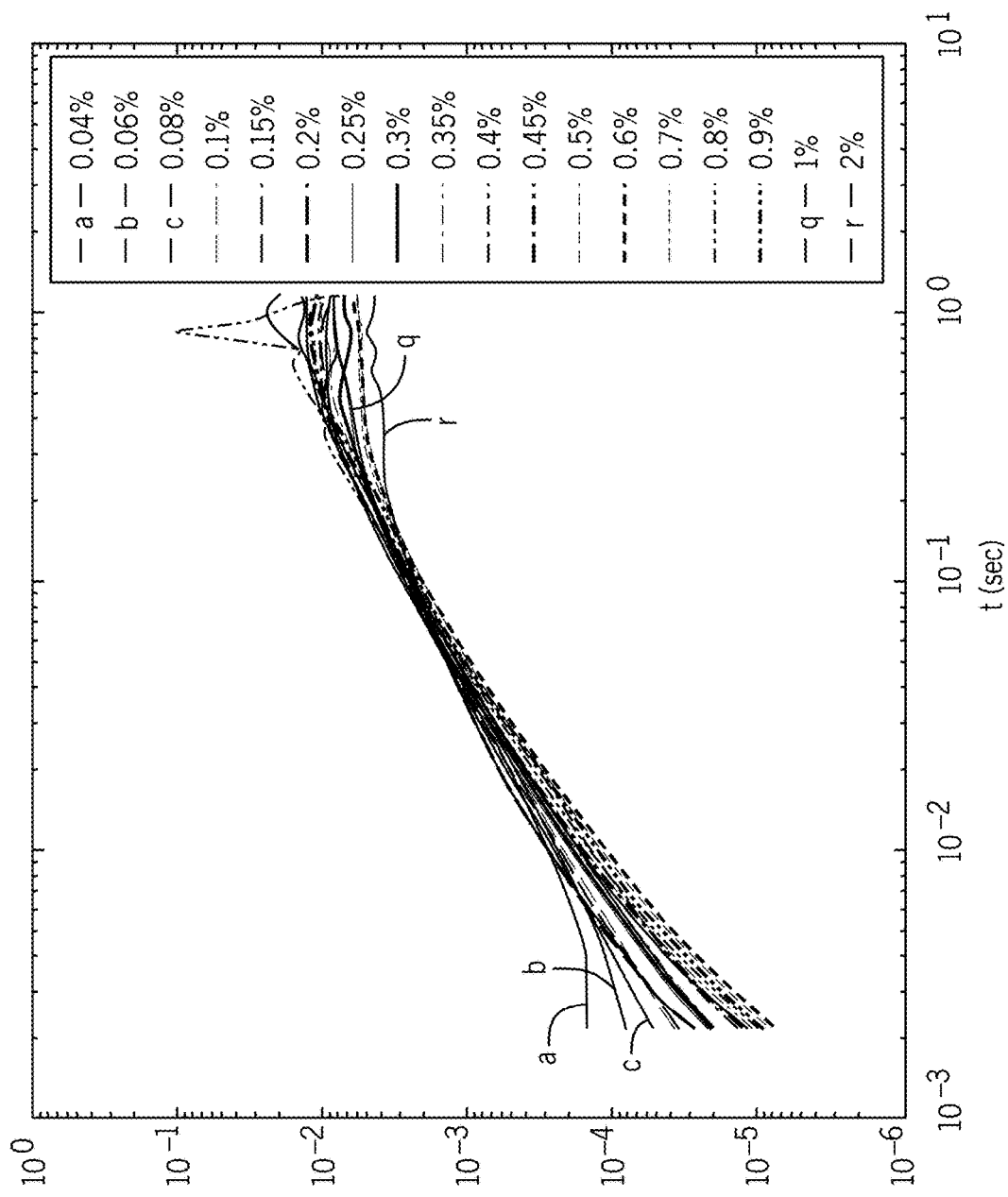
FIG. 8A is plot presenting the results of determination of the compensated MSD, corresponding to the scattering particles in the samples of FIG. 4, obtained with the PSCT-MCRT ray tracing according to an embodiment of the invention.
Figure 8B:
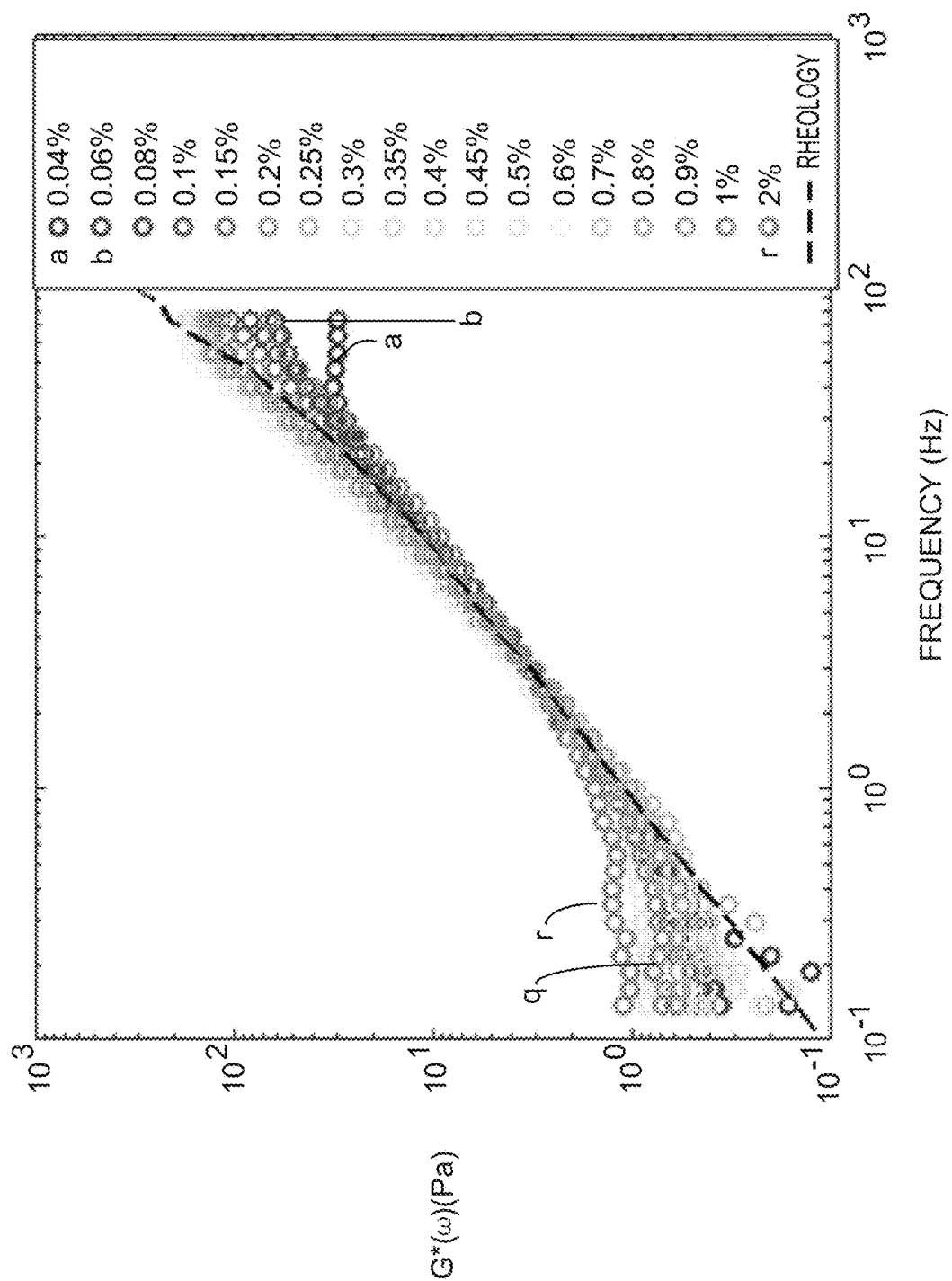
FIG. 8B is a plot presenting the results of determination of the values of compensated complex viscoelastic moduli, corresponding to the samples of FIG. 4, obtained the PSCT-MCRT ray tracing according to an embodiment of the invention.

Phantom Samples: FIG. 8A, plots the MSD of particle dynamics in glycerol suspensions of 90% G-10% W, measured by employing the PSCT-MCRT based optical scattering correction algorithm. The variability between MSD curves over the range of scattering concentrations (0.04%-2%), was significantly reduced compared to the results of FIG. 5 (which employed the DWS formalism). The impact of corrections was more pronounced in the intermediate times and residual small deviations were still observed at very early or long times, corresponding to initial decay and final plateau of $g_2^{exp}(t)$. These mismatches were most likely due to certain experimental factors, as discussed later. FIG. 8B showed the LSR evaluation of $|G^*(\omega)|$ for the 90% G-10% W samples measured by employing optical scattering compensation compared with the corresponding rheometer measurements (dashed line). Compared to FIG. 6, the optical scattering dependence of $|G^*(\omega)|$ curves was significantly reduced by employing the compensation algorithm. Moreover, the scattering compensated moduli corresponding to all scattering concentrations closely corresponded with the measurements of mechanical rheometer. These results demonstrate that while differences in optical properties dramatically modulated the $g_2(t)$ curves, a significant improvement was achieved in the LSR evaluation of viscoelastic moduli when optical scattering variations were compensated for with an embodiment of the algorithm of the invention, as opposed to the direct application of DWS formalism in the estimation of MSD, and calculation of the $|G^*(\omega)|$.

Biological Fluids: In the following discussion, the reference is made to FIGS. 9A and 9B that present plots of speckle decorrelation functions the bovine synovial fluid and the vitreous humor with different concentrations of scattering particles of $TiO_2$, respectively. The concentrations are indicated in plot insets.

The biofluid samples were prepared as follows: the frozen bovine synovial fluid and vitreous humorous (Animal Technologies, Tyler, Tex.) were warmed up to the body temperature (of about 37° C.) in a water bath prior to the LSR imaging. The TiO2 particles were added to these fluids in various concentrations (synovial fluid: 0.08%, 0.1%, 0.15%, and 0.2%, N=4; vitreous humor: 0.08%, 0.1%, 0.15%, N=3) to create scattering signal. In a fashion similar to that described in reference to the phantom samples above, about 1.5 ml of the samples were placed in clear plastic couvettes and about 2 ml were used for measurements with the use of mechanical rheology.

Figure 9A:
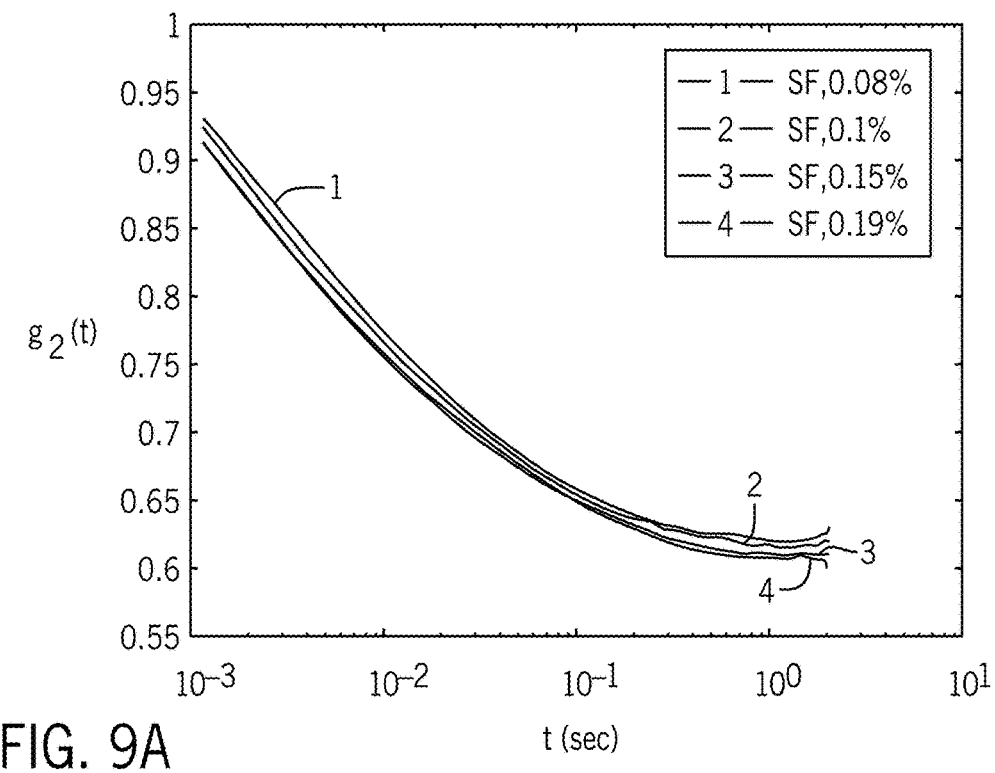
FIGS. 9A and 9B are plots of speckle decorrelation functions the bovine synovial fluid and the vitreous humor with different concentrations of scattering particles of $TiO_2$ obtained according to an embodiment of the invention.
Figure 9B:
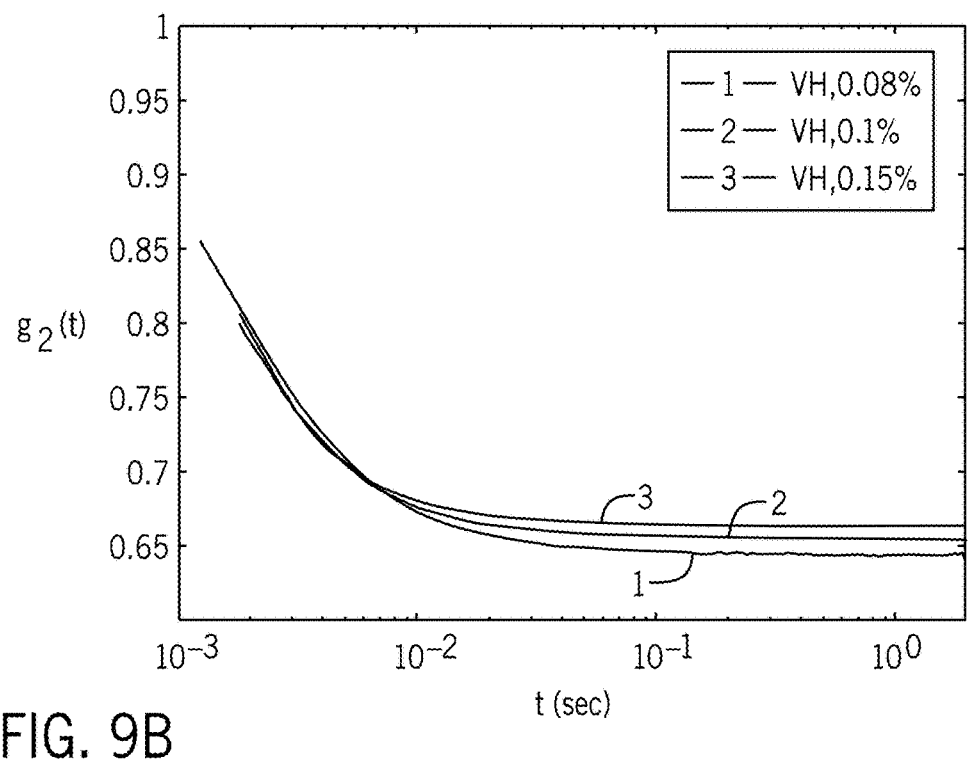

FIGS. 9A and 9B show $g_2^{exp}(t)$ curves measured based on time-varying speckle images of synovial fluid and vitreous humor, respectively. Similar to the glycerol samples, the $g_2^{exp}(t)$ decay accelerated with increased scattering in both cases. Since $g_2^{exp}(t)$ decayed slower for synovial fluid compared to vitreous humor, it was expected that synovial fluid would have a relatively higher modulus. However, it was necessary to correct for the contribution of optical scattering prior to comparing absolute mechanical moduli.

Figure 10A:
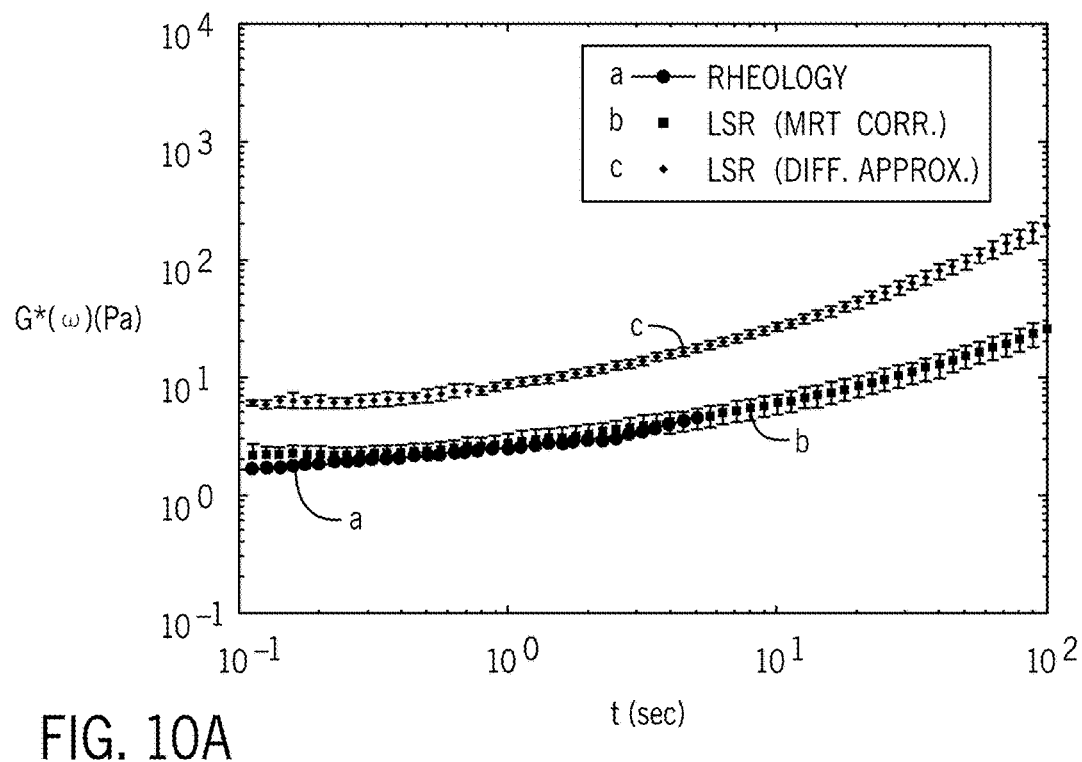
FIGS. 10A and 10B are plots providing comparison between the values of complex viscoelastic moduli obtained based on the mechanical rheological measurements, those based on the LSR measurements under the assumption of diffusion theory, and those based on the LSR measurements and corrected using an embodiment of the method of the invention.
Figure 10B:
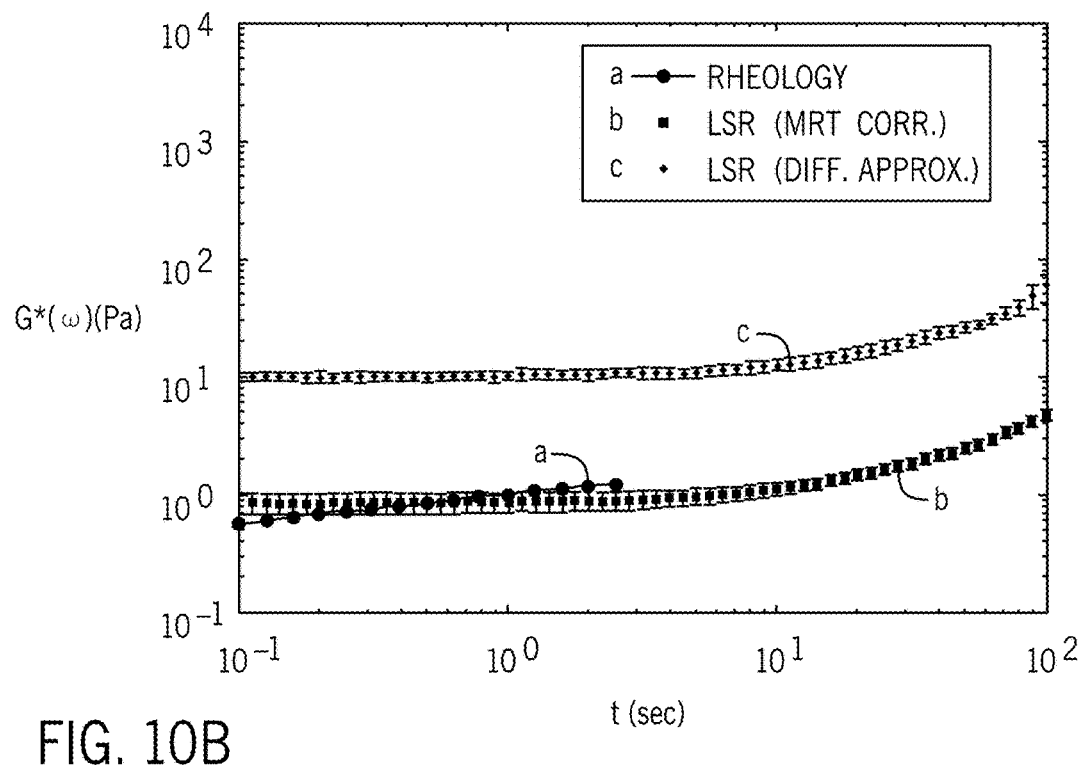

Just like for phantom samples discussed above, for biofluids it was also observed that $g_2(t)$ curves decay faster for samples corresponding to higher concentrations of scattering particles. It is recognized, however, that because both the synovial fluid and the vitreous humor possess a somewhat low viscoelastic modulus, both the LSR-based evaluation and the conventional mechanical rheology based characterization of these samples are rather challenging. On one hand, the conventional mechanical testing of the samples is possible only at relatively low oscillation frequencies (for instance, at less than about 5 to 10 Hz), because at higher frequencies (in excess of 10 Hz or so) the stirring rod inertia produces unreliable data. Accordingly, it may be justified to omit the data acquired with a mechanical rheometer at higher frequencies. On the other hand, the LSR-based determinations are somewhat involved at low frequencies due to rapid speckle evolution, which leads to blurring of images and reduction of speckle contrast. Accordingly, only the initial decay of $g_2(t)$ curves (corresponding to high frequency modulus values) are chosen for representation of viscoelastic behavior, and long-time decorrelation of speckle intensity smears out by artificial raising of the plateau, especially at higher concentrations of scatterers (i.e., for turbid samples approaching the DWS limit such as samples q and r). To partially correct the plateau level, additional processing is performed to restore the contrast through subtracting the background signal, for calculating the $g_2(t)$ function. Consequently, LSR results (curves b of FIGS. 10A and 10B) demonstrate close correspondence with the results of conventional, mechanical rheometric measurement (curves a of FIGS. 10A, 10B) of $G^*(\omega)$ over a limited range at low oscillation frequencies, for the same biofluids. Curves b are obtained based on the LSR measurement data with the use of the PSCT-MCRT algorithm of the invention, while curves c represent the results obtained from the LSR measurement data with the use of the diffusion approximation. The overlapping region (i.e. the region of frequencies within which the results of conventional mechanical rheology substantially equal to the results obtained with the LSR) is smaller for biological fluids as compared to phantom samples. This is pertly due to small complex modulus of biofluids, which inhibits accurate conventional testing of the samples at high frequencies. Moreover, during the measurements performed with the use of conventional mechanical rheology, the strain percentage for biological samples is set to about 1%, as opposed to about 2% for phantom glycerol samples, to eliminate the possibility of damaging the microstructure and changing the mechanical properties. The smaller strain percentage reduces the capability of rheometer in correcting for inertia of the rod at higher frequencies. On the other hand, the LSR methodology is capable of evaluating the modulus over more than three decades. This range can even be extended further by using a higher frame rate and longer acquisition time to increase both low and high frequency limits of the estimated modulus. FIGS. 10A, 10B show the LSR results of $|G^*(\omega)|$ for synovial fluid and vitreous humor, respectively, measured with and without optical scattering correction. The red diamonds represent average $|G^*(\omega)|$ values of synovial fluid and vitreous humor samples of FIGS. 9A, 9B, estimated using LSR based on the DWS expression of Eq. (3), which did not take into account optical scattering variations. The purple squares correspond to the moduli resulted from corrected MSD values, using the modified expression of Eq. (7) derived from the compensation algorithm of the invention. The red and purple error bars stand for the standard error. Also depicted in this figure are the $|G^*(\omega)|$ values measured using a conventional rheometer (black solid line, round markers). It was evident that in the case of LSR with optical scattering correction, $|G^*(\omega)|$ exhibited a close correspondence with conventional mechanical testing. Moreover, $|G^*(\omega)|$ measured using DWS approximation resulted in an offset of about one decade relative to conventional rheometric testing results. This was due to slower decay of speckle intensity temporal autocorrelation curve, caused by relatively low concentration of $TiO_2$ particles as discussed later. From the results of FIGS. 10A, 10B it was clear that synovial fluid had a slightly higher viscoelastic modulus, which was consistent with our initial observation of speckle fluctuations and with standard reference mechanical rheometry. The non-Newtonian behavior of these bio-fluids, reflected in smaller slope of $|G^*(\omega)|$ and lower frequency dependence compared to viscous glycerol solutions, pointed to the complex viscoelastic behavior of bio-fluids relative to glycerol samples. These results established the critical need of compensating for optical scattering properties to enable accurate measurement of viscoelastic moduli from laser speckle patterns and demonstrated the potential of LSR for evaluating the viscoelastic properties of biological fluids.

Optical transparency and clarity of the synovial fluid and the vitreous humor enable changing the optical properties of the samples of these biofluids and facilitated examination of samples with different concentrations of scattering particles. This provided better understanding of optical and mechanical cumulative effects on modulating the speckle dynamics. While the intensity of light scattering at such semitransparent materials, in their native state, and as detected by a photodetector, is rather low, in an embodiment related to that of FIG. 2 higher illumination power and more sensitive detection schemes may enable measurements of samples close to the DLS limit (i.e., samples with low concentration of scatterers) without the intentional manipulating the optical properties of the samples.

The $TiO_2$ tracer particles, used to evaluate biofluids according to the embodiments of the invention, were exogenous scattering centers of known dimension. Thus, the estimation of $G^*(\omega)$ from MSD using the generalize Stokes-Einstein relationship was relatively straightforward. To enable the assessment of viscoelastic parameters of semi-dilute or substantially opaque biological samples (such as, blood, lymph, and mucus, for example) it is important to define a mechanism for estimating the particle size distribution and take into account the poly-dispersed nature of these biofluids.

For the following examples, the aqueous glycerol phantoms were used the properties of which are summarized in Table 2.

TABLE 2

Optical Properties of Aqueous Glycerol Phantoms

| $TiO_2$ | C | | | | | |
|---|---|---|---|---|---|---|
| | 0% | 0.02% | 0.05% | 0.1% | 0.2% | 0.4% |
| 0.05% | $\mu_a = 0$ | $\mu_a = 0.5$ | $\mu_a = 1.2$ | $\mu_a = 2.4$ | $\mu_a = 8.5$ | $\mu_a = 9.8$ |
| | $\mu_s = 8.3$ | $\mu_s = 8.8$ | $\mu_s = 9.5$ | $\mu_s = 10.6$ | $\mu_s = 12.9$ | $\mu_s = 17.5$ |
| | g = 0.61 | g = 0.63 | g = 0.67 | g = 0.71 | g = 0.78 | g = 0.84 |
| 0.1% | $\mu_a = 0$ | $\mu_a = 0.5$ | $\mu_a = 1.2$ | $\mu_a = 2.4$ | $\mu_a = 8.5$ | $\mu_a = 9.8$ |
| | $\mu_s = 16.7$ | $\mu_s = 17.1$ | $\mu_s = 17.8$ | $\mu_s = 19$ | $\mu_s = 21.3$ | $\mu_s = 25.9$ |
| | g = 0.61 | g = 0.62 | g = 0.64 | g = 0.67 | g = 0.71 | g = 0.78 |
| 0.2% | $\mu_a = 0$ | $\mu_a = 0.5$ | $\mu_a = 1.2$ | $\mu_a = 2.4$ | $\mu_a = 8.5$ | $\mu_a = 9.8$ |
| | $\mu_s = 13.4$ | $\mu_s = 33.9$ | $\mu_s = 34.6$ | $\mu_s = 35.7$ | $\mu_s = 38$ | $\mu_s = 42.6$ |
| | g = 0.61 | g = 0.62 | g = 0.63 | g = 0.64 | g = 0.67 | g = 0.71 |
| 0.5% | $\mu_a = 0$ | $\mu_a = 0.5$ | $\mu_a = 1.2$ | $\mu_a = 2.4$ | $\mu_a = 8.5$ | $\mu_a = 9.8$ |
| | $\mu_s = 83.7$ | $\mu_s = 84.1$ | $\mu_s = 84.8$ | $\mu_s = 86$ | $\mu_s = 88.2$ | $\mu_s = 92.8$ |
| | g = 0.61 | g = 0.61 | g = 0.62 | g = 0.62 | g = 0.64 | g = 0.66 |
| 1% | $\mu_a = 0$ | $\mu_a = 0.5$ | $\mu_a = 1.2$ | $\mu_a = 2.4$ | $\mu_a = 8.5$ | $\mu_a = 9.8$ |
| | $\mu_s = 167.4$ | $\mu_s = 167.8$ | $\mu_s = 168.5$ | $\mu_s = 169.6$ | $\mu_s = 172$ | $\mu_s = 176.5$ |
| | g = 0.61 | g = 0.61 | g = 0.62 | g = 0.62 | g = 0.62 | g = 0.64 |
| 2% | $\mu_a = 0$ | $\mu_a = 0.5$ | $\mu_a = 1.2$ | $\mu_a = 2.4$ | $\mu_a = 8.5$ | $\mu_a = 9.8$ |
| | $\mu_s = 33.5$ | $\mu_s = 335$ | $\mu_s = 336$ | $\mu_s = 337$ | $\mu_s = 339$ | $\mu_s = 344$ |
| | g = 0.61 | g = 0.61 | g = 0.61 | g = 0.62 | g = 0.62 | g = 0.62 |

* $\mu_a$ and $\mu_s$ in $mm^{-1}$ unit.
For the sake of comparison, the typical optical properties of oxygenated blood are as follows: $\mu_s$ ~64.47 $mm^{-1}$, $\mu_a$ ~0.3 $mm^{-1}$, g = 0.982 (@ 633 nm). Bile, on the other hand, has the following properties: $\mu_s$ ~42.5 ± 7.5 $mm^{-1}$ and $\mu_a$ ~8.8 ± 1.9 $mm^{-1}$, g = 0.92 (@ 410 nm).

As discussed below, all three approaches (the DWS, the telegrapher approach, and the PSCT-MCRT of the present invention) were used to devise the MSD and the resultant viscoelastic modulus, $|G^*(\omega)|$, from the LSR measurements, and the results were compared with those acquired from the reference standard mechanical rheometry (AR-G2, TA Instruments, MA). All prepared samples (Table 2) were evaluated using the mechanical rheometer, as follows: a sample (2 ml) was placed within the rheometer tool and top plate of 40 mm dia. exerted an oscillatory shear stress upon the sample, with oscillation frequency sweeping the 0.1-100 Hz range to obtain the frequency dependent visco-elastic modulus. Mechanical testing was carried out at 25° C., and 2% strain was applied on the samples.

Example 2

Influence of Optical Scattering on LSR Measurements

Figure 11:
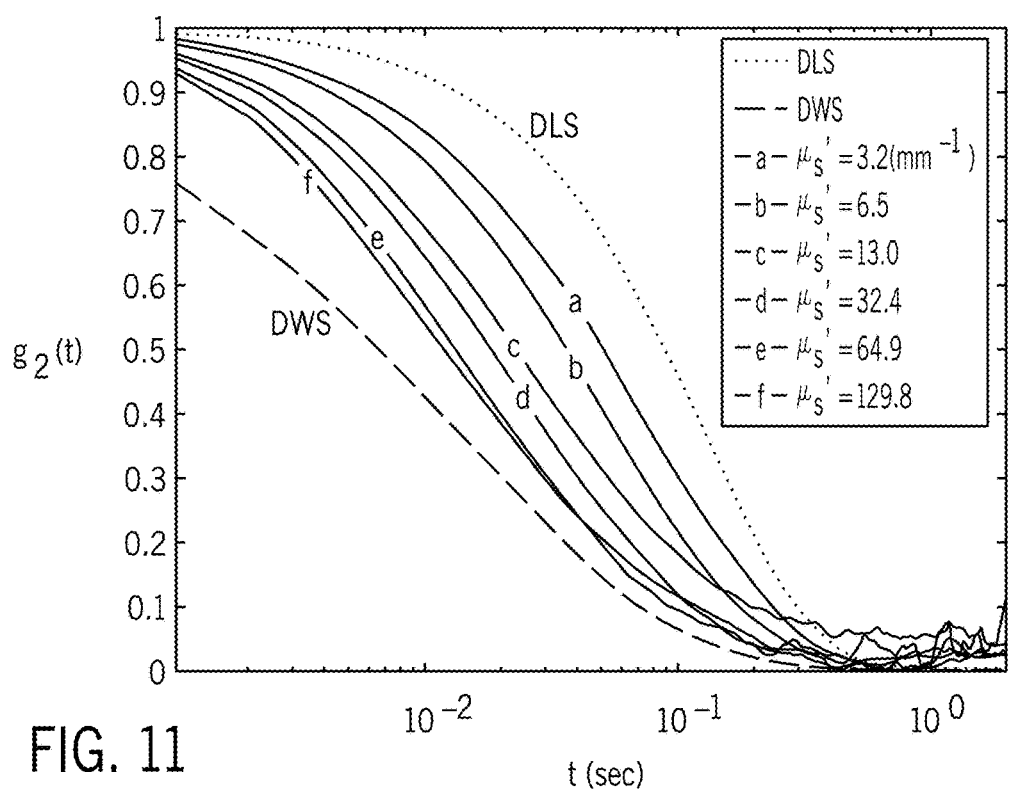
FIG. 11 presents speckle intensity temporal autocorrelation curves for aqueous glycerol suspensions of varying $\mu'_s$. The speckle fluctuations speed up with increasing $\mu'_s$ and accelerate the decay trend of $g_2(t)$ curves.

FIG. 11 displays $g_2(t)$ curves of aqueous glycerol suspensions with identical viscosities but varying concentration of $TiO_2$ scattering particles (0.05%-2%), corresponding to the first column of Table 2. For these samples, $\mu'_s$: 3.2-129 mm$^{-1}$ and $\mu_a \sim 0$ (negligible absorption). In FIG. 11 the dotted and dashed curves corresponds to theoretical $g_2(t)$ curve predicted by Dynamic Light Scattering (DLS) and the DWS formalism for single ($\mu'_s$ very small) and rich multiple scattering ($\mu_a/\mu'_s=0$) scenarios, respectively. Similarly to the results of Example 1, it is observed that the experimental $g_2(t)$ curves for varying scattering properties span the gap between the theoretical limits of single and strong multiple scattering with samples of larger $\mu'_s$ decaying faster. Still, even for $\mu'_s=129.8$ mm$^{-1}$, $g_2(t)$ decays slower than the predictions of diffusion equation for primarily scattering material. This may be related to the shortcomings of the DWS equation in describing the sub-diffusive behavior of back-scattered intensity, as discussed later. The plots of FIG. 11 are similar to our earlier observations (FIG. 4) that the variations in scattering properties modify speckle fluctuations, independent of sample mechanical properties. More specifically, for glycerol suspension of identical viscosities, and consequently similar MSD, the increase in $\mu'_s$ leads to faster temporal speckle fluctuations. As a result, $g_2(t)$ curves of samples with identical mechanical properties exhibit a range of decay rates, tuned purely by scattering properties.

Next, performances of the three approaches, DWS, telegrapher, and PSCT-MCRT in isolating sample mechanics from the influence of varying scattering properties are reported. In the following analysis of the application of DWS, telegrapher, and PSCT-MCRT to isolating sample mechanics from the influence of varying scattering properties is presented. The MSD is deduced from the experimentally evaluated $g_2(t)$ curves of FIG. 11 with the use of dependencies of Eqs. (4), (5), and (7) and substituted in Eq. (8) to calculate the frequency-dependent viscoelastic moduli, $|G^*(\omega)|$, that are displayed in FIGS. 12A, 12B, 12C. The results of the standard mechanical rheometry measurement (denoted as Rheo) are also shown for comparison with the LSR results, in a dashed black curve. For these primarily scattering samples of negligible absorption, both DWS and telegrapher equations (FIGS. 12A, 12B) fail to yield an accurate estimate of viscoelastic properties. In contrast, PSCT-MCRT (FIG. 12C) successfully derives the moduli from speckle intensity temporal autocorrelation curves of FIG. 11.

Figure 12A:
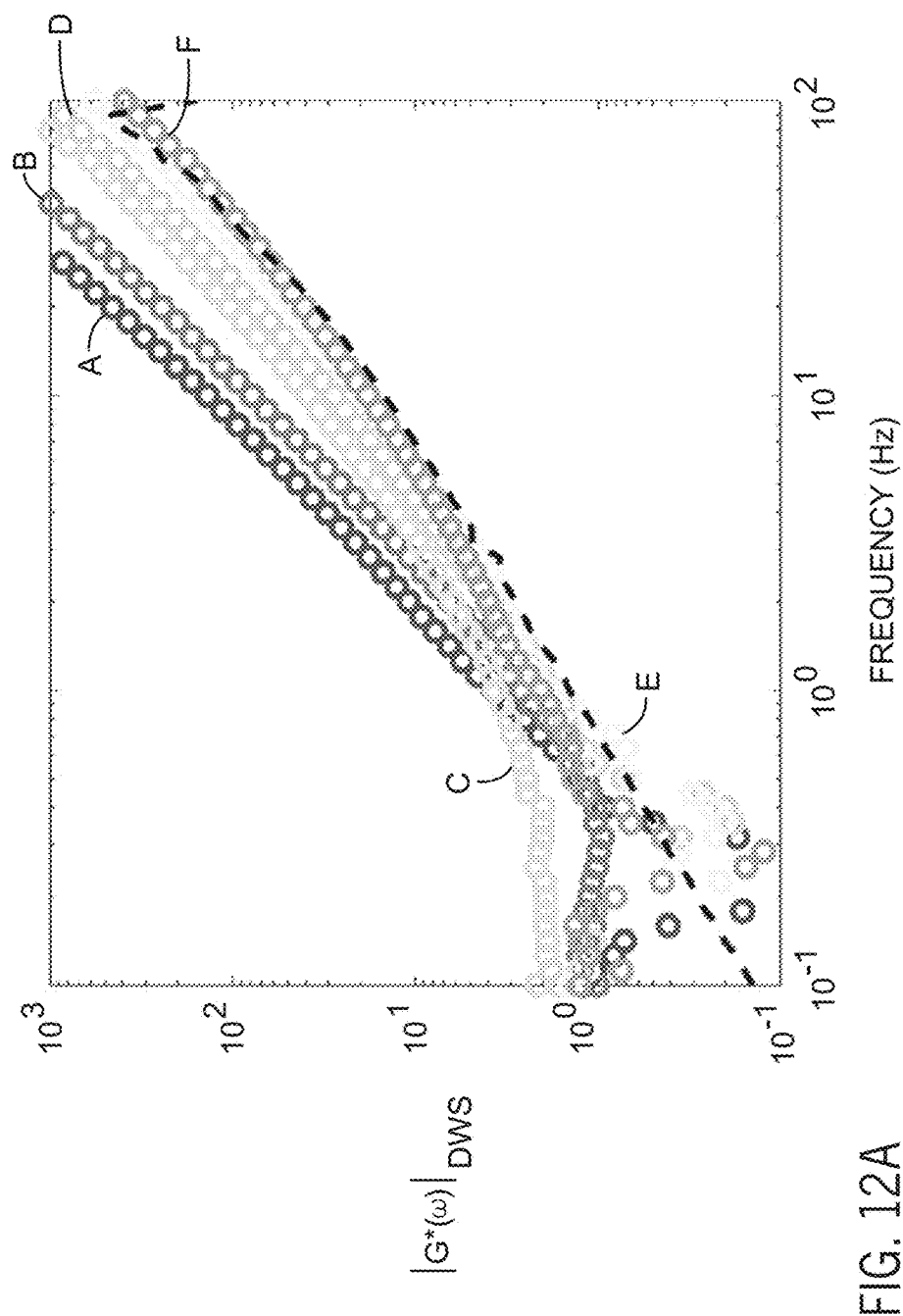
FIGS. 12A, 12B, 12C are plots of viscoelastic moduli, $|G^*(\omega)|$ calculated based on data from $g_2(t)$ curves of FIG. 1, based on the DWS equation, the Telegrapher equation, and the PSCT-MCRT of the invention, respectively. The viscoelastic modulus measured using a conventional rheometer is shown as a black dashed curve.
Figures 12B, 12C:
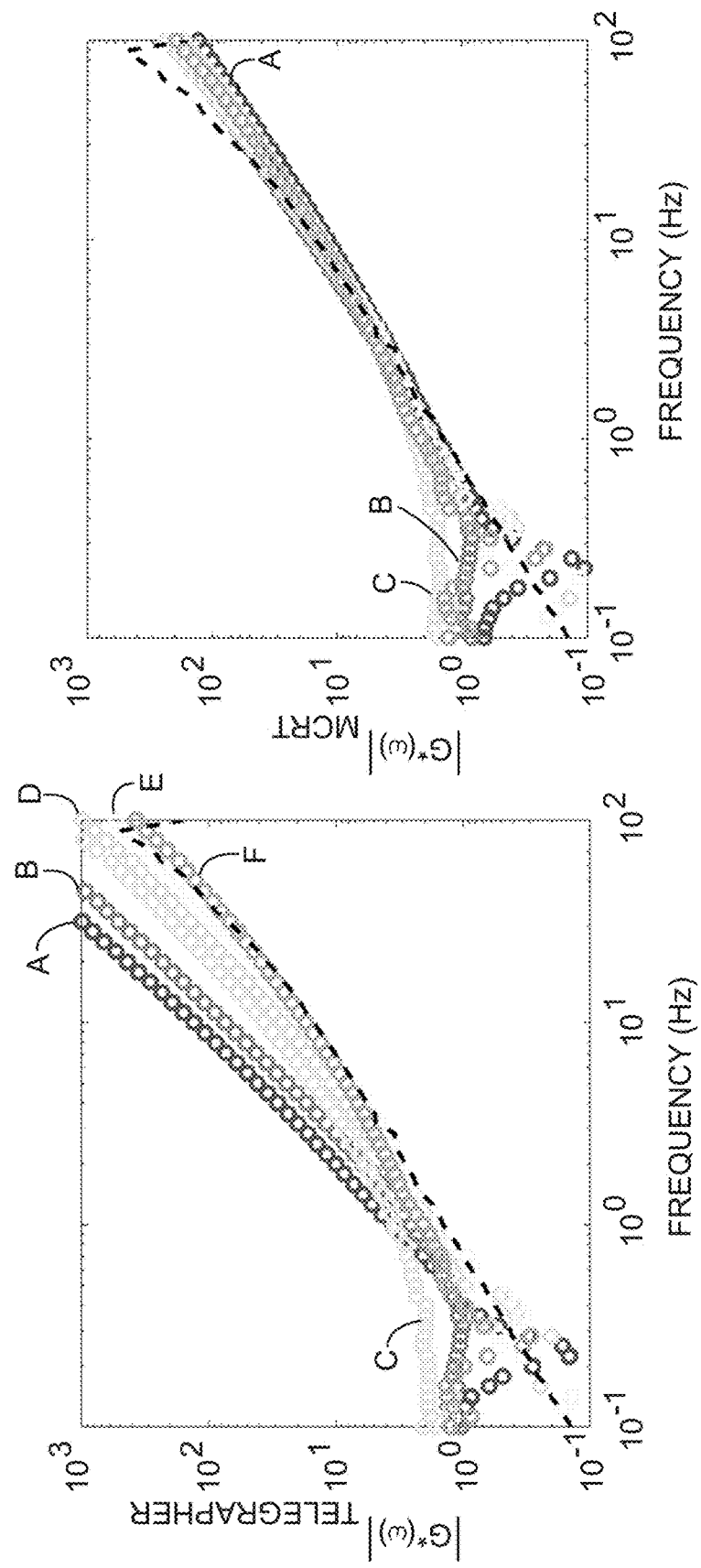

Clearly, $|G^*(\omega)|$ curves obtained from both DWS and telegrapher equations (FIGS. 12A, 12B, respectively) present a considerable deviation from conventional rheology. The failure in accurate extraction of $|G^*(\omega)|$, is drastically aggravated for samples of low to moderate $\mu'_s$ values. In this case, the relatively slower speckle fluctuations, generated by a smaller number of light scattering events, erroneously result in an over-estimation of the viscoelastic modulus. It is only for highly scattering samples (yellow and orange open circles) that the LSR measurements, derived by both DWS (FIG. 12A) and telegrapher equations (FIG. 12B) converge to the results of standard mechanical rheology. Given the comparable performance of the two techniques, it seems that the telegrapher equation fails to improve upon DWS formalism in the backscattering geometry. In stark contradistinction, the PSCT-MCRT approach of the invention succeeds in sufficiently isolating optical scattering contributions to estimate moduli for any arbitrary $\mu'_s$ value (FIG. 12C). The measured $|G^*(\omega)|$ curves corresponding to weakly, moderately, and strongly scattering samples show close correspondence with the results of conventional rheology, especially at intermediate frequencies. At low and high frequency limits, a slight deviation of $|G^*(\omega)|$ curves is observed between LSR and mechanical rheometry potentially caused by speckle contrast artifacts and rheometer inertia limitations, respectively, as discussed later.

Example 3

Influence of Absorption on LSR Measurements

Figure 13:
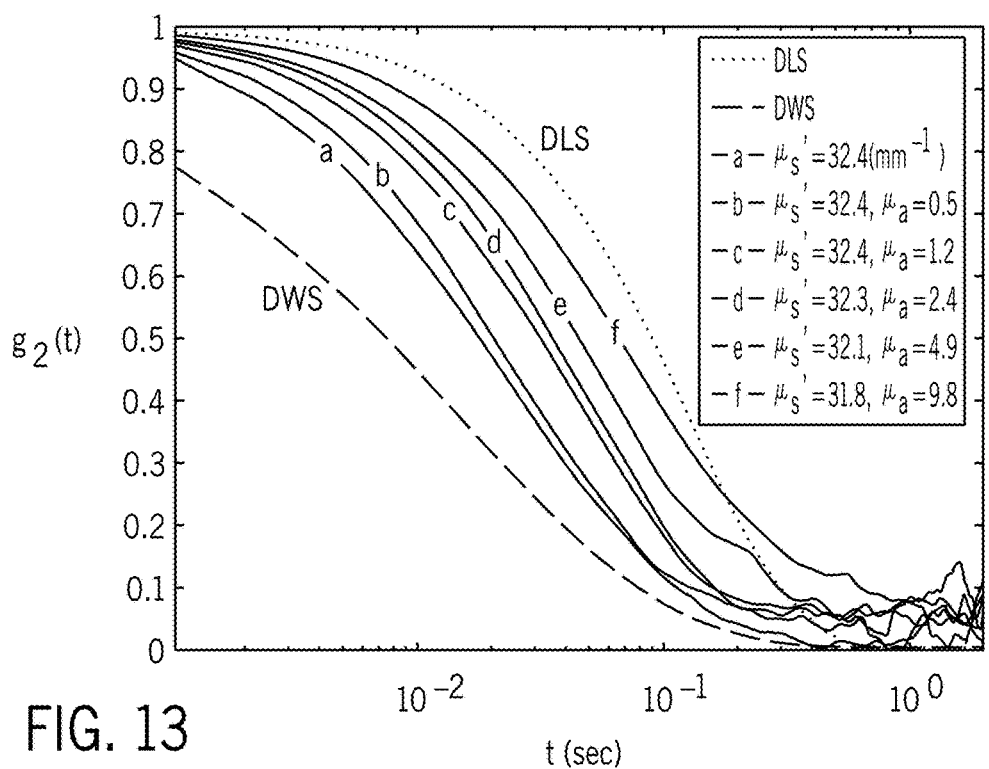
FIG. 13 shows speckle intensity temporal autocorrelation curves for aqueous glycerol suspensions of varying absorption coefficient. As $\mu_a$ increases, speckle fluctuations decelerate, and $g_2(t)$ curves decay slower.

In this Example 3, the optical absorption characteristic of a sample is varied, while scattering properties are maintained constant to assess the collective effects on speckle fluctuations. FIG. 13 displays $g_2(t)$ curves of samples with identical mechanical properties and identical concentration of $TiO_2$ scattering particles (0.5%) mixed with different concentrations of carbon light absorbing nano-powder (0%-0.4%) (the row corresponding to the concentration of TiO2 of 0.5% in Table 2).

Figure 14A:
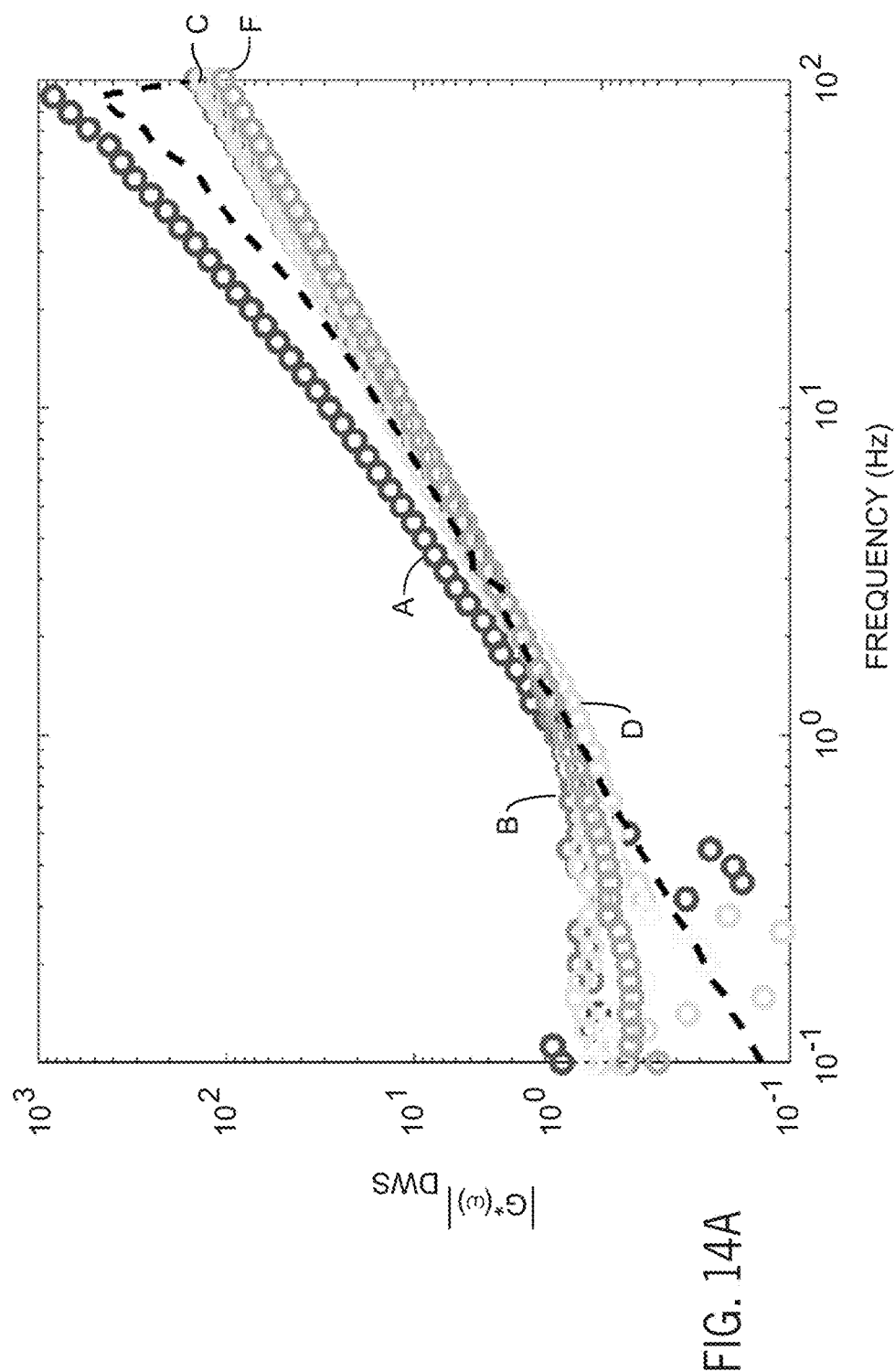
FIG. 14A, 14B, 14C: Viscoelastic modulus, $|G^*(\omega)|$, derived $g_2(t)$ curves of FIG. 13, using the DWS equation, the Telegrapher equation, and the PSCT-MCRT algorithm, respectively, for glycerol suspensions of identical mechanical properties, similar reduced scattering coefficient, $\mu'_s$, but varying absorption coefficient, $\mu_a$. The viscoelastic modulus measured using a conventional rheometer is shown as a black dashed curve. It is clear that DWS and telegrapher approaches are capable of correcting for the influence of variations in $\mu_a$. PSCT-MCRT performs well for any arbitrary set of optical properties.
Figures 14B, 14C:
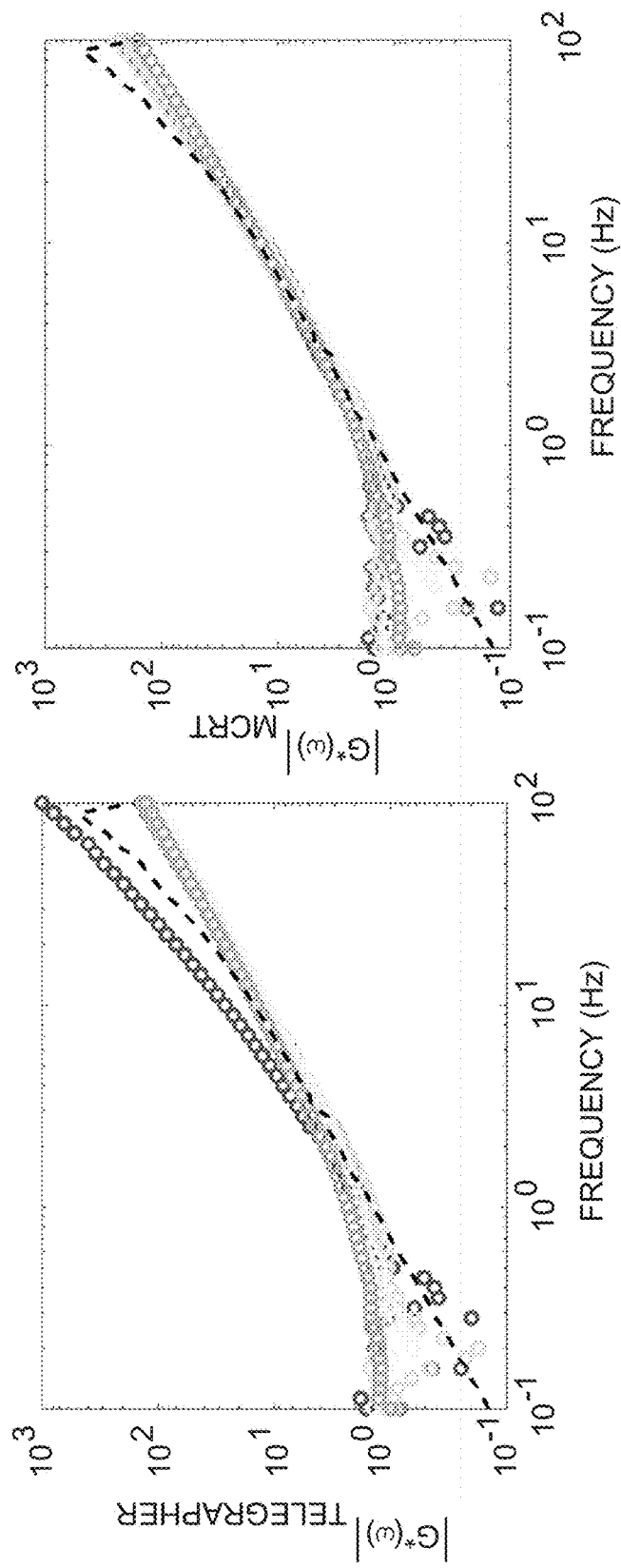

It is observed that the variation of absorption properties greatly influences the $g_2=(t)$ curve. As absorption coefficient increases, temporal speckle intensity fluctuations slow down, likely due to elimination of longer optical paths, which involve a larger number of scattering events. FIGS. 14A, 14B, 14C display the resulting $|G^*(\omega)|$, obtained from the $g_2(t)$ curves of FIG. 11 according to the procedure described in Example 2.

Results of FIGS. 14A through 14C indicate that both DWS and telegrapher formalisms are capable of accounting for changes in speckle intensity fluctuations, caused by variation in absorption properties. As compared to FIGS. 12A through 12C, which clearly display the errors induced in estimated $|G^*(\omega)|$ values by scattering variations, with the addition of absorbing particles it appears that both DWS and telegrapher formalisms are fairly resilient to absorption-induced adjustment of speckle intensity fluctuations, in cases when $\mu_a$ is non-negligible. However, in both FIGS. 14A and 14B, the $|G^*(\omega)|$ estimated from LSR measurements for the sample with $\mu'_s=32.4$ mm$^{-1}$ and $\mu_a=0$ exhibits a significant deviation from the rheology measurements. The capability of the DWS and telegrapher algorithms in extracting the MSD and consequently the $|G^*(\omega)|$, in the presence of non-negligible absorption stems from the fact that both Eqs. (4) and (5) incorporate the influence of absorption in the term $\mu_a/\mu'_s$ and predict that for a fixed $\mu'_s$, increase in $\mu_a$, leads to slower speckle intensity temporal fluctuations. The telegrapher algorithm does not present a tangible superiority upon DWS equation. In FIG. 14C, $|G^*(\omega)|$ derived via the PSCT-MCRT approach of the invention is displayed, which also effectively compensates for the attributes of absorption variation from the final $|G^*(\omega)|$ curves in all cases. Just as in FIGS. 12A through 12C, small deviations are still present at high/low frequency limits due to experimental artifacts discussed later.

Example 4

Combined Influence of Scattering and Absorption on LSR Measurements

Figure 15A:
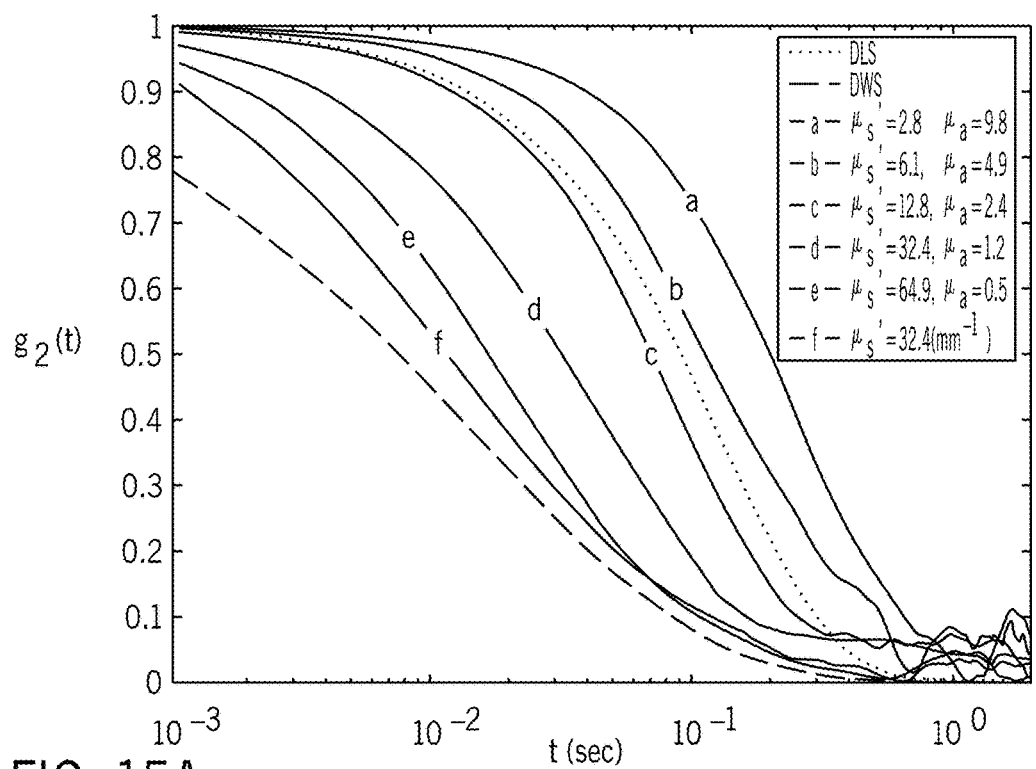
FIGS. 15A, 15B show speckle intensity temporal autocorrelation curves, $g_2(t)$ for samples of varying $\mu'_s$ and $\mu_a$.

So far we have separately investigated the influence of scattering and absorption variations on speckle intensity fluctuations, by keeping one of the $\mu'_s$ and $\mu_a$ fixed, and modifying the other. To obtain the results in FIGS. 15A and 15B, both $\mu'_s$ and $\mu_a$ are varied simultaneously. At first, in FIG. 15A, we consider the temporal speckle fluctuation adjustments as a consequence of increasing the $\mu'_s$ while reducing the $\mu_a$ ($\mu'_s\uparrow,\mu_a\downarrow$) (minor diagonal in Table 2). In the second scenario in FIG. 15B, speckle fluctuations are modified by simultaneously increasing both $\mu'_s$ and $\mu_a$ ($\mu'_s\uparrow,\mu_a\uparrow$) (major diagonal in Table 2). In FIG. 15A, the differences of ($\mu'_s,\mu_a$) pairs cause a significant variation in the experimentally measured $g_2(t)$. For the strongly scattering sample of negligible absorption ($\mu'_s\sim129.8$ mm$^{-1}$ and $\mu_a\sim0$, orange curve), light scatters multiple times before being detected and minute displacements of scattering particles, involved in each light path, accumulate and induce a rapidly decaying $g_2(t)$ curve. By gradually adding small amounts of absorbing particles and reducing the scattering concentration, for instance in samples with ($\mu'_s=64.9$ mm$^{-1}$, $\mu_a=0.5$ mm$^{-1}$), and ($\mu'_s=32.4$ mm$^{-1}$, $\mu_a=1.2$ mm$^{-1}$), and ($\mu'_s=12.8$ mm$^{-1}$, $\mu_a=2.4$ mm$^{-1}$), long optical paths are ultimately absorbed and $g_2(t)$ curves slow down, proportionally. Notice that for these curves, $\mu_a/\mu'_s$ values are equal to 0.007, 0.037, and 0.187, respectively. Thus, as the exponent in Eq. (4) predicts, by gradual growth of $\mu_a/\mu'_s$ ratio, $g_2(t)$ shows a proportionate slow down. Finally, for weakly scattering samples of strong absorption, ($\mu'_s=6.1$ mm$^{-1}$, $\mu_a=4.9$ mm$^{-1}$) and ($\mu'_s=2.8$ mm$^{-1}$, $\mu_a=9.8$ mm$^{-1}$), most rays scatter only a few times, due to the sparse distribution of scattering centers. Besides, strong absorption extensively eliminates long optical paths that propagate through the medium. The collective effects of weak scattering and strong absorption render a low intensity scattered signal of sub-diffusive characteristics. For these samples, the $\mu_a/\mu'_s$ ratio rises to 0.8 and 3.5, respectively, indicating that the attributes of absorption dominates that of scattering and the underlying assumptions of both DWS and telegrapher equations are at the verge of breakdown. It is observed that the $g_2(t)$ curves decay even slower than the theoretical limit for optically dilute single-scattering medium. This excessive slow-down behavior is likely due to increase in carbon particles' concentrations, which has a three-fold impact on speckle intensity fluctuations. Firstly, it leads to strong absorption, which eliminates the long optical paths and slows downs the speckle intensity fluctuations. Additionally, since carbon particles are susceptible to clustering and agglomeration at high concentrations, average particle diameter increases and impedes the $g_2(t)$ decay accordingly. Finally, the potentially increased average particle size leads to larger scattering anisotropy, as seen in Table 2.

Figure 15B:
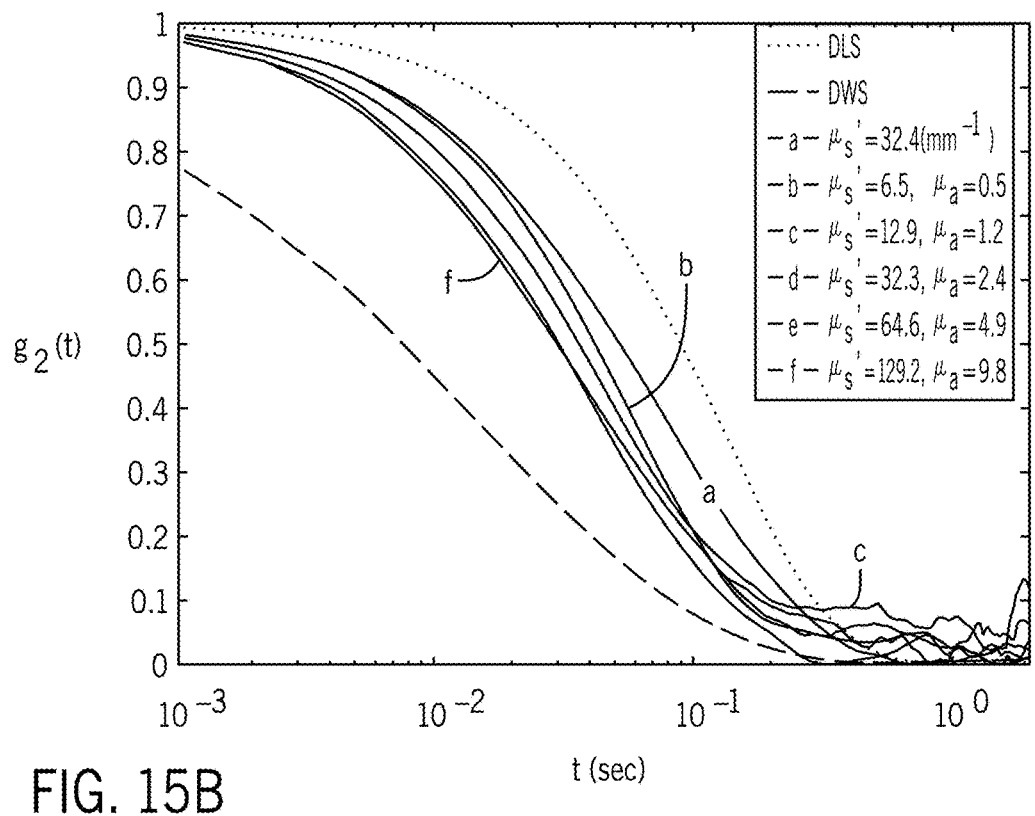

As opposed to FIG. 15A, in FIG. 15B $g_2(t)$ curves follow a very similar decay trend, despite considerable difference in optical properties. In this panel, optical properties of samples are chosen so that $\mu'_s$ and $\mu_a$ vary proportionally. Increasing $\mu'_s$ is expected to increase the number of received long optical paths of larger decorrelation. However, simultaneous increase of $\mu_a$ trims these light paths and cancels out the influence of larger $\mu'_s$. Thus, the collective influence of increasing both $\mu'_s$ and $\mu_a$ leads to only small changes in speckle fluctuations, which is reflected by the fact that the parameter $\mu_a/\mu'_s$ varies minimally between 0.074 and 0.093, ensuing only minute shifts in $g_2(t)$.

FIGS. 16A through 16C display the resulting viscoelastic moduli, extracted from all $g_2(t)$ curves of FIG. 15A, using the DWS and telegrapher equations and the PSCT-MCRT algorithm, respectively. Viscoelastic moduli corresponding to samples of low to moderate $\mu_a$ represent close agreement with the results of conventional rheology in all three cases. However, for weakly scattering samples of strong absorption, $|G^*(\omega)|$ values derived using DWS, Eq. (4), show the closest agreement with the results of conventional rheology. The $|G^*(\omega)|$ values extracted using PSCT-MCRT exhibit a minor but non-negligible offset with respect to the reference standard rheometry, and the curves obtained using telegrapher equation fail altogether in cases of strong absorption.

Revisiting FIG. 15A explains that while excessive slow down of $g_2(t)$ curves for samples with highest concentrations of Carbon nano-powder is likely caused by particle agglomerations, the DWS formalism ascribes this entirely to the optical properties and the large $\mu_a/\mu'_s$ values. At this limit of strong absorption, the diffusion approximation is no longer valid and Eq. (4) predicts a $g_2(t)$ curve behavior that is unreliably even slower than DLS approximation for single scattering. Nonetheless compensating for speckle slow-down based on $\mu_a/\mu'_s$, ratio effectively restores the MSD and the consequent $|G^*(\omega)|$ values to match the results of conventional rheology. The telegrapher equation, on the other hand, is inclined to over-estimate the $|G^*(\omega)|$ whenever scattering is highly anisotropic. This issue is further aggravated when absorption is strong and modulus is magnified erroneously (FIG. 16B). Finally, in these weakly scattering samples with low $TiO_2$ concentration, carbon particles aggregation heavily modifies the average particle size. Therefore, while PSCT-MCRT accurately evaluates the particles' MSD, lack of sufficient knowledge on the net increase in particles' radius (Eq. (7)) leads to an over-estimated $|G^*(\omega)|$, in this case, as seen in FIG. 16C. The underlying causes of these observations are discussed in more detail below.

FIGS. 17A, 17B, 17C display results of $|G^*(\omega)|$ derived from the $g_2(t)$ curves of FIG. 15B, using the same three approaches. Both DWS and telegrapher approaches can successfully isolate the contribution of optical properties in samples, for which $\mu'_s$ and $\mu_a$ are non-negligible and proportional, as shown in FIG. 17A, 17B, respectively. Similarly to FIGS. 12A, 12B, 12C, the extracted $|G^*(\omega)|$ curve exhibits a drastic offset for weakly scattering samples with negligible absorption ($\mu'_s=3.2$ mm$^{-1}$ and $\mu_a=0$). In contradistinction, the PSCT-MCRT results, shown in FIG. 17C, exhibit a close agreement with conventional rheology in all cases.

Discussion

Examples 2 through 4 address the influence of optical absorption and scattering on temporal speckle intensity fluctuations and clarify that alterations in sample optical properties complicate the analysis of the speckle intensity autocorrelation curve, $g_2(t)$, for extracting the MSD of light scattering particles, and induce inaccuracies in the estimated viscoelastic moduli. Results of FIGS. 11, 13, 15A, 15B clearly illustrate that for samples of identical viscosities, $g_2(t)$ is still modulated by tuning $\mu_a$ and $\mu'_s$. In particular, FIG. 11 demonstrates that increasing $\mu'_s$ leads to faster speckle decorrelation, for glycerol solutions of identical viscosities. Here, $\mu'_s$ is raised by increasing scattering particles concentration. This causes a net growth in the number of scattering events within the illuminated volume and renders the speckle pattern more sensitive to even the smallest Brownian displacements of scattering particles, $\mu'_s$ may also increase by reducing the anisotropy parameter, g. In this case, larger scattering angles (Doppler shifts) are more likely and speckle fluctuations are more perceptive to the displacement of scattering particles. On the contrary when $\mu_a$ is elevated by tuning the carbon nano-powder concentration, longer light paths terminate due to absorption. As a result, rate of speckle fluctuations is reduced, FIG. 13. Therefore, the overall decay trend of the $g_2(t)$ curves may slow down by either reducing the $\mu'_s$ or increasing the $\mu_a$ and, as FIG. 15A, 15B indicate, the ratio $\mu_a/\mu'_s$ often sufficiently explains how the $g_2(t)$ decay trend is adjusted by optical properties. In the current study, Mie theory is exploited to obtain $\mu_a$, $\mu_s$, and g based on the size, and concentration of $TiO_2$ and carbon particles, as well as their relative refractive indices to that of the background glycerol solution at the source wavelength of 632 nm. In these calculations, the actual particle sizes of $TiO_2$ and carbon particles, derived from DLS-based particle sizing experiment, are used to ensure the accuracy of the resulting optical properties. These properties are indeed responsible for majority of variations between speckle intensity autocorrelation curves seen in FIGS. 11, 13, and 15. At the same time, results of our independent DLS-based particle sizing measurements reveal that carbon particles are prone to agglomeration at higher concentrations, and give rise to slightly larger average particle sizes. The shifts in average particle size is likely responsible for the excessive slowing down of $g_2(t)$ curves even beyond the DLS limit, in weakly scattering and strongly absorbing samples of FIG. 15A.

In the current study, sample optical properties are tuned based on the range of values relevant to common bio-fluids. In biological systems, $\mu'_s$ is related to the size distribution of cellular nuclei and organelles, and the concentrations of connective fibers and collagen, and $\mu_a$ is primarily dependent on blood perfusion, lipid and water content, and presence of biological pigments such as melanin and bilirubin. For instance, the optical properties of oxygenated blood are $\mu_s$~64.47 mm$^{-1}$, $\mu_a$~0.3 mm$^{-1}$, and g=0.982 (@633 nm), and for bile $\mu_s$~42.5±7.5 mm$^{-1}$ and $\mu_a$~8.8±1.9 mm$^{-1}$, and g=0.92 (@410 nm). In order to conduct LSR in tissue, it is necessary to experimentally evaluate optical properties, prior to further analysis of the MSD and subsequently $|G^*(\omega)|$. Here we demonstrated the potential of extracting both $\mu'_s$ and $\mu'_s$ from temporally averaged speckle frames and the total remittance profile of the photons. To this end, the radial diffuse remittance profile was fitted to a model curve derived from steady state diffusion theory and $\mu_a$ and $\mu'_s$ were extracted. The results of the current study, however, indicate that independent determination of both parameters may not be necessary and evaluating the parameter $\mu_a/\mu'_s$, as a whole adequately simplifies the problem. This ratio is related to transport albedo, given by $a'=\mu'_s/(\mu'_s+\mu_a)$, and $\mu_a/\mu'_s=1/a'-1$. The transport albedo is in turn closely correlated with the degree of depolarization of back-scattered light and a more simplified approach may be sufficient to extract this ratio based on the polarization properties of the received speckle signal. In a more realistic scenario, such as in tissue, apart from optical properties, the poly-dispersity of scattering particles influences the speckle fluctuations. Large scattering particles pose slower Brownian displacements, where as smaller particles exhibit faster thermal motions, and modify the decay rate of $g_2(t)$ curve, accordingly. Moreover interactions between live scattering centers complicate the analysis of speckle intensity fluctuations in biological systems. For more in-depth analysis of scattering features in tissue, additional hardware capabilities may be embedded to incorporate the polarization dependent analysis of diffused back-scattered light or angle-resolved low coherence radiation to more accurately describe particle size distribution within tissue.

Analysis of the acquired speckle frame series show that variations in optical properties not only adjust the speckle intensity fluctuation rate, but also modify the speckle contrast, which is closely related to the $g_2(t)$ plateau. Here, fast acquisition at 964 fps (exposure time~1 ms) is used to capture the rapid speckle fluctuations and avoid temporal speckle blurring. However, highly scattering samples with weak absorption exhibit exceedingly rapid speckle fluctuations which restrain the speckle temporal contrast. Moreover, samples with different optical properties pose distinct backscattered signal level. Since the CMOS sensor bit depth is limited, the spatial speckle contrast reduces as $\mu'_s$ increases due to CMOS pixel saturation, and improves by increasing $\mu_a$. The poor contrast, potentially affects the long time behavior of $g_2(t)$ curves by raising the plateau level.

The current study compares the performance of three approaches used to isolate the influence optical and mechanical properties on speckle intensity temporal fluctuations, to derive particle MSD from $g_2(t)$ curves. The extent of particle MSD is in turn related to the sample viscoelastic modulus through the GSER (Eq. (8)). Among the three approaches used here, the DWS formalism provides the simplest and most mathematically tractable expression for speckle intensity fluctuations as shown in Eq (4). The results presented in FIGS. 12A through 12C, 14A through 14C, 16A through 16C, and 17A through 17C demonstrate that for typical biological tissues, with non-negligible weak to moderate absorption features ($\mu_a \neq 0$), and highly anisotropic scattering (g~0.9), the simple DWS expression and a partial knowledge of optical properties via $\mu_a/\mu'_s$ ratio enables the accurate evaluation of the MSD and subsequently estimation of $|G^*(\omega)|$ via the GSER equation.

However, the DWS formalism fails whenever absorption is negligible, since the modifying factor of $\mu_a/\mu'_s \rightarrow 0$. In this case, as shown in FIGS. 12A, 14A, and 17A, the final $|G^*(\omega)|$ curves derived from the MSD, exhibit a bias with respect to the results of standard mechanical testing. The magnitude of this bias is proportional to the deviation of the optical properties from that of a strongly scattering medium.

In the other extreme, for weakly scattering samples of strong absorption, when $\mu_a/\mu'_s$ is markedly large, Eq. (4) predicts that the $g_2(t)$ curve would slow down indefinitely. Such behavior is not practically feasible, since the received light has scattered at least once and the $g_2(t)$ curve is not expected to decay any slower than the function of Eq. (2), which is obtained from the DLS formalism for single-scattered light intensity autocorrelation function. The generally cited criterion for validity of DWS formalism is that the mean free path should be sufficiently smaller than the absorption length, or equivalently $\mu_a/\mu'_s<0.1$. From FIGS. 14A, 16A, and 17A, it is evident that the DWS formalism provides an accurate description of particle MSD and subsequently the $|G^*(\omega)|$ in moderately absorbing media. The competency of the DWS equation is explained by the broad distribution of received rays in the back-scattering geometry, which is composed of both sub-diffusive ballistic and snake photons as well as diffusive components. The DWS equation is plausibly accurate in describing the behavior of the diffusive part, equivalent to the early decay of $g_2(t)$. On the other hand, it falls short in describing the long-time decay of the $g_2(t)$, related to shorter path lengths with fewer scattering events. However, the long time plateau of $g_2(t)$ curve is often affected by speckle contrast variability as described above. The early, intermediate, and long time decay of $g_2(t)$ curve translate into high, mid, and low speed particles displacements, MSD, respectively. The MSD at these time scales in turn correspond to $|G^*(\omega)|$ measured at high, intermediate, and low frequencies, respectively. Thus, it is evident that the DWS formalism permits a precise account of viscoelastic modulus in the range of moderate to high frequencies for highly scattering samples with moderate absorption.

As opposed to DWS approach, the telegrapher equation requires not only the $\mu_a/\mu'_s$ ratio, but also the anisotropy factor, g, to retrieve the particles' MSD from $g_2(t)$ as seen in Eq. (5). Despite incorporating this extra piece of information, the telegrapher equation does not provide any improvement upon DWS in most cases (FIGS. 12A through 12C, 14A through 14C, and 17A, 17B). Comparing the viscoelastic modulus in FIGS. 16A, 16B reveals that the telegrapher equation performs worse than DWS in the presence of strong absorption, especially if scattering is highly anisotropic. This is an unexpected observation since the telegrapher equation has been originally proposed to overcome the limitations of the diffusion equation in treating scattering anisotropy and strong absorption. Close examination of $g_2^{Tel}(t)$ in Eq. (5) reveals that for small $x=k_0^2n^2\langle\Delta r^2(t)\rangle+3\mu_a/\mu'_s$, this equation follows a similar trend to that of Eq. (4). This explains the similarities between estimated viscoelastic modulus derived via the DWS approach and telegrapher equation, in cases when optical scattering is dominant. At intermediate x values ($0.5<x<1$), the $g_2^{Tel}(t)$ decay rate increases slightly (compared to $g_2^{DWS}(t)$) for large $g_2$(anisotropic scattering). Finally for ($x>1$), which often corresponds to short optical paths with fewer number of scattering events, $g_2^{Tel}(t)$ breaks down similar to DWS approach. For weakly scattering samples of strong absorption in FIG. 16B, $\mu_a/\mu'_s=0.8$ and 3.5, respectively, and x is large even at initial decay times. Since scattering is highly anisotropic as well, (g=0.71, and 0.84, respectively), telegrapher equation predicts that $g_2(t)$ is rapidly decaying function of x. However, in reality elevated $\mu_a$ slows down the $g_2(t)$ decay rate. As a result, if telegrapher equation is exploited to analyze the experimentally evaluated $g_2(t)$ curves in the presence of both strong absorption and scattering anisotropy, MSD tends to be underestimated and the final $|G^*(\omega)|$ values are over-estimated, as seen in FIG. 16B. Thus, telegrapher equation proves unreliable and falls short of the intent to improve upon DWS.

The results in FIGS. 12A through 12C, 14A through 14C, 16A through 16C and 17C, demonstrate that the use of the embodiment of the PSCT-MCRT algorithms of the invention, that takes into account the entire set of experimental geometry, optical properties, and polarization effects provide the most accurate estimate of the MSD and the sample viscoelasticity for any arbitrary choice of optical properties. The PSCT-MCRT approach, although computationally intensive, accurately tracks photons within the turbid medium of known optical properties and computes the total momentum transfer $Y=\Sigma q^2/(2k_0^2)$. As a result, in all cases it provides superior accuracy over DWS and telegrapher equations. FIGS. 12C, 14C, 16C, and 17C clearly depict the advantage of using this numerical approach in accurate calculation of viscoelastic modulus, $|G^*(\omega)|$, for any arbitrary set of optical properties. The only slight exception appears in FIG. 16C, in which PSCT-MCRT approach overestimates the viscoelastic modulus for weakly scattering samples of strong absorption. At these weakly scattering samples with lower $TiO_2$ concentrations and higher carbon nano-powder content, carbon particles dominantly determine the average particle radius. In this case, PSCT-MCRT approach correctly deduces particles MSD from experimentally evaluated $g_2(t)$ curves using Eq. (4). However, lack of sufficient information about the effective particle size, due to particle agglomeration, and substituting the nominal particle radius (200 nm) in Eq. 8 results in a slight offset of the evaluated modulus compared to the standard rheometry measurements. This observation indicates the importance of more robust particle sizing method to improve the accuracy of LSR measurements.

Implementation of the embodiments of the invention demonstrated that by tuning the sample's optical scattering and absorption, temporal speckle intensity fluctuations are modulated independently from viscoelastic properties. Therefore, the influence of sample's optical properties needs to be isolated in order to correctly derive the MSD and subsequently estimate the viscoelastic modulus from LSR measurements. These findings indicate that in the presence of moderate optical absorption, the simple DWS formalism based on diffusion theory closely mirrors the more computationally intensive PSCT-MCRT approach in extracting the MSD for the typical set of optical properties, and yields accurate estimates of sample viscoelastic moduli. These findings obviate the need for going through a more complex route of Monte-Carlo Ray Tracing, whenever noticeable absorption features exist and the ratio $\mu_a/\mu'_s\ll1$. While the DWS expression proves adequate for interpreting the LSR measurements in turbid media with typical optical properties of tissue, the DWS formalism fails in the case of low to moderate scattering whenever absorption is negligible. The current development on correcting for the influence of optical properties helps to significantly improve the performance and accuracy of LSR to measure the mechanical properties of tissue.

The following notes are in order. References made throughout this specification to "one embodiment," "an embodiment," "a related embodiment," or similar language mean that a particular feature, structure, or characteristic described in connection with the referred to "embodiment" is included in at least one embodiment of the present invention. Thus, appearances of these phrases and terms may, but do not necessarily, refer to the same implementation. It is to be understood that no portion of disclosure, taken on its own and in possible connection with a figure, is intended to provide a complete description of all features of the invention.

In addition, the following disclosure may describe features of the invention with reference to corresponding drawings, in which like numbers represent the same or similar elements wherever possible. It is understood that in the drawings, the depicted structural elements are generally not to scale, and certain components may be enlarged relative to the other components for purposes of emphasis and clarity of understanding. It is also to be understood that no single drawing is intended to support a complete description of all features of the invention. In other words, a given drawing is generally descriptive of only some, and generally not all, features of the invention. A given drawing and an associated portion of the disclosure containing a description referencing such drawing do not, generally, contain all elements of a particular view or all features that can be presented is this view, for purposes of simplifying the given drawing and discussion, and to direct the discussion to particular elements that are featured in this drawing. A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this detail in the drawing may be implied unless the context of the description requires otherwise. In other instances, well known structures, details, materials, or operations may be not shown in a given drawing or described in detail to avoid obscuring aspects of an embodiment of the invention that are being discussed. Furthermore, the described single features, structures, or characteristics of the invention may be combined in any suitable manner in one or more further embodiments.

If the schematic logical flow chart diagram is included, the depicted order and labeled steps of the logical flow are indicative of only one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method.

While the description of the invention is presented through the above examples, those of ordinary skill in the art understand that modifications to, and variations of, the illustrated embodiments may be made without departing from the inventive concepts disclosed herein. Furthermore, disclosed aspects, or portions of these aspects, may be combined in ways not listed above. Overall, embodiments of the invention demonstrate the capabilities of the LSR for non-contact evaluation of the bulk mechanical properties of biofluids and probing heterogeneity in viscoelastic properties. These capabilities of the LSR can be advantageously exploited, for example, for studying the regionally-varying rheological properties of biofluids induced by variations in concentration of macromolecules (such as collagen and hyaluronic acid) and electrolytes, for instance in a vitreous body. The invention as recited in claims appended to this disclosure is intended to be assessed in light of the disclosure as a whole, including features disclosed in prior art to which reference is made.

What is claimed is:

1. A method for determining a viscoelastic modulus of a tissue sample possessing at least one of an optical scattering characteristic and an absorption characteristic with the use of laser speckle rheology (LSR), the method comprising:
    acquiring, from the tissue sample, using an optical detector coupled to a computer processor on a computing device and executing computational steps on a computer readable medium, data sets representing time evolution of speckle associated with the sample irradiated with light from a light source;
    determining, by the computing device, an optical property of said tissue sample based at least on a radial profile of flux determined from the acquired data sets; and
    calculating, by the computing device, a mean square displacement (MSD) value based on intensity temporal autocorrelation curve, which curve describes the time evolution of speckle based on the determined optical property and sample viscoelasticity.

2. A method according to claim 1, wherein the determining an optical property includes calculating an absorption coefficient and a reduced scattering coefficient based at least on a radial profile of flux determined from averaged-over-time data from the data sets.

3. A method according to claim 1, further comprising calculating a total momentum transfer distribution associated with photon scattering at the optically scattering tissue sample based on the optical property.

4. A method according to claim 3, wherein the calculating a total momentum transfer distribution includes calculating a total momentum transfer distribution based on absorption and reduced scattering coefficients determined, with a diffusion approximation, from the radial profile of flux.

5. A method according to claim 3 including polarization-sensitive correlation transfer Monte-Carlo ray tracing enabling a simulation of a correlation transport of polarized light by calculating a total momentum transfer distribution based on the absorption and reduced scattering coefficients that are determined, with a diffusion approximation, from the radial profile of flux.

6. A method according to claim 1, further comprising deriving a simulated Laplace transform of a total momentum transfer function corresponding to the optical property of the tissue sample.

7. A method according to claim 6, further comprising determining fitting parameters for a curve fitted to the simulated Laplace transform based on statistics of photons scattered by the optically scattering tissue sample.

8. A method according to claim 7, wherein the determining fitting parameters include determining fitting parameters based on the simulated Laplace transform of the total momentum transfer associated with photon scattering at the optically scattering tissue sample.

9. A method according to claim 1, wherein the calculating MSD value includes calculating a speckle intensity temporal autocorrelation function and determining an MSD value from said speckle intensity temporal autocorrelation function.

10. A method according to claim 1, further comprising calculating a frequency-dependent value representing logarithmic slope of the MSD value as a function of time.

11. A method according to claim 10, further comprising determining a frequency-dependent value of complex viscoelastic modulus characterizing the optically scattering tissue sample.

12. A method according to claim 1, wherein said tissue includes a biological fluid.

13. A method according to claim 1, wherein said tissue includes at least one of a cerebrospinal fluid (CSF), mucus, synovial fluid, vitreous humor, blood, lymph, and an organ lubricant.

14. A method for determining a viscoelastic modulus of a biological fluid characterized by at least one of optical scattering and absorption with the use of laser speckle rheology (LSR), the method comprising:
    acquiring, from the biological fluid, using an optical detector coupled to a computer processor on a computing device and executing computational steps on a computer readable medium, data sets representing time evolution of speckle associated with the biological fluid irradiated with laser light;
    calculating, by the computing device, an intensity decorrelation function based on the acquired data sets;
    determining, by the computing device, parameters of a fitting curve, for the intensity decorrelation function, based on the Laplace transform of a momentum transfer distribution associated with photon scattering by the biological fluid and calculated based on at least an absorption and a reduced scattering coefficient characterizing distribution of optical scatterers in the biological fluid; and deriving, by the computing device, a value of the viscoelastic modulus based on a closed algebraic form of the fitting curve.

15. A method according to claim 14, wherein the determining parameters of a fitting curve includes integrating the momentum transfer distribution over photon paths.

16. A method according to claim 14, wherein the determining parameters of a fitting curve includes determining said parameters based at least on a radial profile of flux derived from the acquired data sets.

17. A method according to claim 14, wherein the deriving a value includes calculating a corrected mean square displacement (MSD) value corresponding to the closed algebraic form of the fitting curve.

18. A method according to claim 14, wherein said biological fluid includes at least one of a cerebrospinal fluid (CSF), mucus, synovial fluid, vitreous humor, blood, lymph, and an organ lubricant.

* * * * *